United States Patent
Verhulst et al.

(10) Patent No.: US 11,800,301 B2
(45) Date of Patent: Oct. 24, 2023

(54) NEURAL NETWORK MODEL FOR COCHLEAR MECHANICS AND PROCESSING

(71) Applicant: Universiteit Gent, Ghent (BE)

(72) Inventors: Sarah Verhulst, Ghent (BE); Deepak Baby, Martigny (CH); Fotios Drakopoulos, Pylos Messinia (GR); Arthur Van Den Broucke, Knokke-Heist (BE)

(73) Assignee: Universiteit Gent, Ghent (BE)

( * ) Notice: Subject to any disclaimer, the term of this patent is extended or adjusted under 35 U.S.C. 154(b) by 196 days.

(21) Appl. No.: 17/611,597

(22) PCT Filed: Jun. 9, 2020

(86) PCT No.: PCT/EP2020/065893
§ 371 (c)(1),
(2) Date: Nov. 16, 2021

(87) PCT Pub. No.: WO2020/249532
PCT Pub. Date: Dec. 17, 2020

(65) Prior Publication Data
US 2022/0248148 A1     Aug. 4, 2022

(30) Foreign Application Priority Data

Jun. 9, 2019 (EP) .................................. 19179210
Apr. 1, 2020 (EP) .................................. 20167522

(51) Int. Cl.
*H04R 25/00* (2006.01)
*A61N 1/36* (2006.01)
(Continued)

(52) U.S. Cl.
CPC ....... *H04R 25/507* (2013.01); *A61N 1/36038* (2017.08); *G06N 3/04* (2013.01);
(Continued)

(58) Field of Classification Search
CPC ................. H04R 25/507; H04R 25/606; A61N 1/36038; G06N 3/04; G06N 3/08; G06N 3/063
See application file for complete search history.

(56) References Cited

U.S. PATENT DOCUMENTS 9,302,103 B1 * 4/2016 Nirenberg ............ A61N 1/3605
2007/0005348 A1   1/2007 Klefenz
(Continued)

FOREIGN PATENT DOCUMENTS

| CN | 107 845 389 A | 3/2018 |
| CN | 108053829 A | 5/2018 |
| CN | 109862498 A | 6/2019 |

OTHER PUBLICATIONS

PCT International Search Report dated Oct. 2, 2020 in connection with PCT International Patent Application No. PCT/EP2020/065893.
(Continued)

*Primary Examiner* — Suhan Ni
(74) *Attorney, Agent, or Firm* — Amster, Rothstein & Ebenstein LLP

(57) ABSTRACT

A method and hearing device (100) for emulating cochlear processing of auditory stimuli are disclosed, in which a multilayer convolutional encoder-decoder neural network (10) sequentially compresses and then decompresses a time-domain input comprising a plurality of samples. At least one nonlinear unit for applying a nonlinear transformation is mimicking a level-dependent cochlear filter tuning associated with cochlear mechanics and outer hair cells. Other described modules cover inner-hair-cell and auditory-nerve fiber processing. A plurality of shortcut connections (15) is directly forwarding inputs between convolutional layers of the encoder (11) and the decoder (12). An output layer (14) is generating, for each input to the neural network, N output sequences of cochlear response parameters corresponding to N emulated cochlear filters associated with N different center frequencies to span a cochlear tonotopic place-frequency map. A transducer (105) of the hearing device converts output sequences generated by the neural network (10) into auditory-stimulus dependent audible time-varying pressure signals, or basilar-membrane vibrations, inner-hair-cell potentials, auditory-nerve firing patterns or population coding thereof for auditory or augmented hearing applications.

15 Claims, 13 Drawing Sheets

(51) Int. Cl.
*G06N 3/04* (2023.01)
*G06N 3/063* (2023.01)
*G06N 3/08* (2023.01)

(52) U.S. Cl.
CPC .............. *G06N 3/063* (2013.01); *G06N 3/08* (2013.01); *H04R 25/606* (2013.01)

(56) References Cited

U.S. PATENT DOCUMENTS

2018/0014130 A1* 1/2018 Lunner .................. A61F 11/06
2019/0164052 A1 5/2019 Sung et al.
2020/0201435 A1* 6/2020 Ciccarelli .............. G06F 18/22

OTHER PUBLICATIONS

PCT Written Opinion dated Oct. 2, 2020 in connection with PCT International Patent Application No. PCT/EP2020/065893.
Lai Ying-Hui et al: "A Deep Denoising Autoencoder Approach to Improving the Intelligibility of Vocoded Speech in Cochlear Implant Simulation", IEEE Transactions On Biomedical Engineering, IEEE Service Center, Piscataway, NJ, USA, vol. 64, No. 7, Jul. 1, 2017 (Jul. 1, 2017), pp. 1568-1578, XP011653914.
Zadak J et al: "An Application of Mapping Neural Networks and a Digital Signal Processor for Cochlear Neuroprostheses", Biological Cybernetics, Springer Verlag, Heidelberg, DE, vol. 68, No. 6, Apr. 1, 1993 (Apr. 1, 1993), pp. 545-552, XP000362213.
China National Intellectual Property Administration, "First Review Notice of Observations", issued in Chinese Patent Application No. 202080042340.4, which is a counterpart to U.S. Appl. No. 17/611,597, dated Jul. 26, 2023, 15 pages (10 pages of English Translation of Office Action and 5 pages of original Office Action).

* cited by examiner

NEURAL NETWORK MODEL FOR COCHLEAR MECHANICS AND PROCESSING

CROSS-REFERENCE TO RELATED APPLICATIONS

This application is a U.S. national stage entry under 35 U.S.C. § 371 of PCT International Patent Application No. PCT/EP2020/065893, filed Jun. 9, 2020, which claims priority to European Patent Application No. 19179210.0, filed Jun. 9, 2019 and European Patent Application No. 20167522.0, filed Apr. 1, 2020, the contents of each of which are incorporated herein by reference in their entirety.

FIELD OF THE INVENTION

The present invention generally relates to the field of audio processing. More specifically, it relates to methods and devices for auditory processing of sound by emulating the human auditory system.

BACKGROUND OF THE INVENTION

The human cochlea (or, inner ear) is an active, nonlinear system which transduces sound into cochlear travelling waves which can be characterized as basilar membrane (BM) displacement or velocity. Modeling these cochlear travelling waves can be useful for better understanding the mechanisms of hearing, compensating for hearing impairments and even to improve machine hearing applications.

However, characterizing cochlear travelling waves in terms of BM displacement is a non-trivial computational problem, as traveling-wave descriptions have to capture several aspects of cochlear processing such as its level-dependent tuning (Q), the relationship between tonotopy and Q, as well as the coupling of the cochlear filters. One popular approach is to approximate the cochlea as a nonlinear transmission line (TL) model which discretizes the space along the BM length and describes each section as a system of ordinary differential equations (ODEs) that describes the system behavior of a specific section (or tonotopic location) along the BM.

In addition, TL models represent the cochlea as a cascaded system, i.e., the response of a cochlear section also depends on the responses of all previous cochlear sections. This makes these models computationally expensive since it is not possible to parallelize the computations involved in solving the coupled ODEs in cascaded cochlear models. This computational complexity poses a design constraint on using this type of cochlear models for hearing-aid and machine-hearing applications which require short computation latencies (in the order of ms).

In addition, none of the existing NN-based auditory models capture the properties of the auditory periphery up to the level of the inner-hair-cell and auditory-nerve processing.

Consequently, there is a need for improved cochlear modeling systems that are easy to compute and have short latencies, while capturing the key nonlinear, coupling and frequency-selectivity properties of (human) cochlear processing. The resulting modeling system would ensure that machine-hearing devices, robotics applications and methods for assisted/augmented hearing are based on human-realistic normal or hearing-impaired audio-processing. While human-realistic processing can so far only be achieved by slow-to-compute TL models, improved cochlear modeling systems that reach the performance of state-of-the-art TL models, but at a reduced computational complexity are highly desirable. Specifically, their computational complexity and speed should match that of other fast, but more basic cochlear processing models commonly used in auditory applications such as CAR-FAC, MEL, Gammatone, or Gammachirp.

SUMMARY OF THE INVENTION

It is an object of embodiments of the present invention to provide good methods and systems for emulating cochlear processing of auditory stimuli, good hearing aids using such methods and systems for modeling hearing, as well as methods for assisting in hearing, using such modeling methods.

It is an advantage of embodiments of the present invention to provide good modeling systems and methods that allow accurate modeling in a fast way.

It is an advantage of embodiments of the present invention that a transformation of an auditory stimulus into cochlear basilar membrane vibrations is accurately emulated.

It is an advantage of embodiments of the present invention that human auditory system characteristics such as auditory stimulus level and frequency-dependent (frequency) selectivity is accurately captured via a large number of output sequences generated by the neural network that correspond to an equal number of emulated cochlear filters.

It is an advantage of embodiments of the present invention that a wide range of auditory systems across human and non-human animal beings can be emulated in an accurate manner.

It is an advantage of embodiments of the present invention that normal hearing and hearing impairments can be accurately emulated.

It is an advantage of embodiments of the present invention that the processing can be individualized to hearing impairment characteristics of the individual i.e. frequency-specific patterns of outer-hair-cell, inner-hair-cell or auditory-nerve fiber damage patterns, and hence can be used in backpropagation methods which aim to compensate for a single aspect, or combinations of aspects, of hearing damage.

Methods and devices in accordance with the present invention can be advantageously used for improving currently available hearing aids.

It is an advantage of embodiments of the present invention that they may allow faster emulation when implemented on devices that support (massively) parallelized computation, for instance on multiple processing elements (PEs) such as graphical processing units (GPUs).

It is an advantage of embodiments of the present invention that the methods and devices for emulating cochlear processing, can be easily implemented and integrated into hearing devices, hearing aids, automatic speech recognition systems and machine hearing applications.

Embodiments of the present invention have the advantage that they can be implemented with short processing delays so as to afford live or close-to-live audio processing capabilities.

It is an advantage of embodiments of the present invention that they can be easily combined with a wide range of available speech recognition software or algorithms, for which they may be used as a speech or audio signal preprocessing module.

Methods and devices in accordance with some embodiments of the present invention can perform reliably in the presence of noise affected auditory stimuli.

The above objective is accomplished by methods and devices according to the present invention.

The present invention relates to a computer-implemented method for emulating cochlear processing of auditory stimuli. The method comprises the step of providing a multilayer convolutional encoder-decoder neural network including an encoder and a decoder, each comprising at least a plurality of successive convolutional layers, successive convolutional layers of the encoder having increasing strides with respect to an input to the neural network to sequentially compress the input and successive convolutional layers of the decoder having increasing strides with respect to the compressed input from the encoder, to sequentially decompress the compressed input, each convolutional layer comprising a plurality of convolutional filters for convolution with an input to the convolutional layer to generate a corresponding plurality of activation maps as outputs. The neural network also comprises at least one nonlinear unit for applying a nonlinear transformation to the activation maps generated by at least one convolutional layer of the neural network, and the nonlinear transformation is mimicking a level-dependent cochlear filter tuning, for example response, associated with cochlear mechanics and outer hair cells. Also included in the neural network, a plurality of shortcut connections provided between the encoder and the decoder is forwarding inputs to a convolutional layer of the encoder directly to at least one convolutional layer of the decoder. The neural network furthermore comprises an input layer for receiving inputs to the neural network, and an output layer for generating, for each input to the neural network, N output sequences of cochlear response parameters corresponding to N emulated cochlear filters associated with N different center frequencies to span a cochlear tonotopic place-frequency map, wherein the cochlear response parameters of each output sequence are indicative of a place-dependent time-varying vibration of a cochlear basilar membrane. The method also comprises providing at least one input sequence of predetermined length indicative of a time-sampled auditory stimulus, and applying the same at least one input sequence to the input layer of the neural network to obtain the N output sequences of cochlear response parameters.

The term "predetermined length" as used herein, refers to the length of the input sequence to the model. In some embodiments, the length of the input sequences is the same for the models of the different stages. In some embodiments, the length of the input sequences is different between the models of the different stages. While the models are preferably trained on fixed-length sequences, they still have the ability to work with variable lengths of input sequences in the same way.

The input may comprise one audio input sequence, or one or more cochlear responses as inputs. N is an integer of one or more, preferably 2 or more.

The method optionally comprises the step of summing (or combining) the obtained N output sequences to generate a single output sequence of cochlear response parameters (herein also referred to as population coding). Summing (or combining) the obtained N output sequences of the cochlea allows for obtaining a single output sequence (waveform) that shares the same representation as the input sequence and can be played back in the same way. This way, one can listen to the sound that is produced by different cochlear models (both normal-hearing and hearing-impaired) to also experience how a hearing-impaired periphery "sounds" like. In some embodiments, the method comprises the step of obtaining a single output sequence, and optionally playing it back. In some embodiments, the method comprises the step of comparing different cochlear models (for example normal-hearing and hearing-impaired) by listening to the output sequences.

In some embodiments, the method is used in an invertible cochlear filter bank, preferably in a hearing-aid application. An invertible cochlear filter bank allows to analyze one single input sequence to N output sequences and then re-synthesize these output sequences (by summing or combining in a more elaborate way) to create a single input sequence again. Such a filter bank also provides the ability to process the N output sequences in a more detailed, frequency-dependent way, in order to receive a processed input sequence. This is useful for hearing-aid applications and could also relate to a closed-loop approach, for example for outer-hair-cell and/or auditory-nerve damage compensation.

The nonlinear unit may apply the nonlinear transformation as an element-wise nonlinear transformation, preferably a hyperbolic tangent. The neural network may comprise a plurality of nonlinear units for applying a nonlinear transformation to the activation maps generated by each convolutional layer of the neural network.

A number of convolutional layers of the encoder may equal a number of convolutional layers of the decoder.

The neural network may comprise shortcut connections between each convolutional layer of the encoder and a corresponding one convolutional layer of the decoder. At least some of the shortcut connections may be provided between the first of the successive convolutional layers of the encoder and the last of the successive convolutional layers of the decoder. The neural network may comprise shortcut connections between each convolutional layer of the encoder and a corresponding one convolutional layer of the decoder. The neural network may comprise shortcut connections between each but the last one convolutional layer of the encoder and a corresponding one convolutional layer of the decoder.

The increasing strides for the successive convolutional layers of the encoder with respect to the input to the neural network may be equal to the increasing strides for the successive convolutional layers of the decoder with respect to the compressed input, thereby matching each convolutional layer of the encoder with a corresponding one convolutional layer of the decoder to transpose a convolution operation of the convolutional layer of the encoder.

A number of samples for the at least one input sequence may equal a number of cochlear response parameters in each output sequence. The at least one input sequence may comprise a pre-context and/or a post-context portion, respectively preceding and/or succeeding a plurality of input samples indicative of the auditory stimulus. In some embodiments of the invention, the method further may comprise a cropping step for cropping each of the generated output sequences to contain a number of cochlear response parameters that is equal to a number of input samples of the plurality of input samples indicative of the auditory stimulus.

In another aspect, the present invention also relates to a method for determining a plurality of weight parameters associated with the neural network in any one emulation method as described above, i.e. a training method. The neural network weight parameters are determined by carrying out the following steps. Providing a training dataset which comprises a plurality of training input sequences in a first step, wherein each training input sequence comprises a plurality of input samples indicative of a time-sampled auditory stimulus. Providing, in a second step, a biophysically accurate validation model for cochlear processing, preferably a cochlear transmission line model, for example cochlear BM processing by a preferred (cochlear) transmission line model, a degree of accuracy of which is evaluated with respect to experimentally measured cochlear response parameters indicative of place-dependent time-varying basilar membrane vibrations in accordance with a cochlear tonotopic place-frequency map. Then N training output sequences are generated for each training input sequence, wherein each of the N training output sequences is associated with a different center frequency of the cochlear tonotopy map. In a further step, the emulation method is performed using the neural network of any of the emulation methods and using training input sequences to generate corresponding emulated sequences of cochlear response parameters for the neural network, wherein the neural network generates the N output sequences with respect to the same cochlear tonotopy map as the cochlear tonotopy map for the validation model. Next, a deviation is evaluated between the emulated sequences and the training output sequences, which, together, are arranged as training pairs. The emulated sequence and the training output sequence of each training pair is associated with a same training sequence. Then an error backpropagation method is used for updating the neural network weight parameters, which also comprise the weight parameters associated with each convolutional filter. Optionally, the neural network weight parameters are retrained for a different set of neural network hyperparameters to further reduce the deviation, wherein the different set of neural network hyperparameters includes one or more of: a different nonlinear transformation applied by the at least one nonlinear unit, a different number of convolutional layers in the encoder and/or decoder, a different number of convolutional filters in any one convolutional layer of the neural network, a different length as the predetermined length for the input sequence, a different configuration of shortcut connections, and optionally a different size of the convolutional filters.

The method may comprise the steps of providing a modified validation model reflecting cochlear processing, for example BM, IHC or auditory-nerve processing, subject to a hearing impairment, and retraining the neural network weight parameters for the modified validation model or a combination of the validation model and the modified validation model. A combination of the validation model and the modified validation model may include a difference or a correction to compensate the hearing impairment with respect to the output sequences associated with different center frequencies of the cochlear tonotopy map.

As used herein, the term "hearing impairment" covers hearing loss in every stage of the auditory periphery. The term "hearing impairment" may refer to the conventional outer-hair-cell damage as well as to presbycusis, inner-hair-cell damage, or auditory-nerve synapse damage (cochlear synaptopathy or deafferentation). In some embodiments, the hearing impairment as used herein refers to only outer-hair-cell (OHC) damage. In some embodiments, the hearing impairment as used herein refers to both outer-hair-cell (OHC) and/or inner-hair-cell damage or loss and auditory nerve fiber (ANF) damage.

As used herein, the term "cochlear synaptopathy" refers to hearing damage to auditory-nerve (AN) fiber synapses. For example, noise exposure can cause a selective loss of auditory nerve fibers even when hearing thresholds are retained at normal levels. Cochlear synaptopathy has been also described as hidden hearing loss, as it is not thought to be detectable using standard measures of audiometric threshold. Evidence from human and animal studies suggest that this "hidden" hearing loss impacts robust encoding of speech in every-day listening conditions and understanding of speech in noise. Because synaptopathy occurs earlier in time than outer-hair-cell deficits in the ageing process, it is expected that a large population of people with self-reported hearing difficulties (but normal audiograms) or those with impaired audiograms might suffer from synaptopathy.

In yet another aspect, the present invention relates to a data processing device comprising means for carrying out the method steps as described above, the data processing device comprises input means for receiving at least one input sequence indicative of an auditory stimulus, a plurality of multiply-and-accumulate units for performing convolution operations between the convolutional filters of a convolutional layer and the inputs to the convolutional layer, and a memory unit for storing at least the neural network weight parameters.

The processing device may be a specially designed processing unit such as an ASIC, or may be a dedicated, energy-efficient machine learning hardware module, for instance a convolution accelerator chip, suitable for portable and embedded applications, e.g. battery-powered applications. The processing device may comprise a systolic array of processing elements for a distributed computation of convolutions via a systolic data flow on the array. Such data flow on the array of processing elements may be row-stationary and the data flow mapping may be flexible, for instance layer-size dependent. The processing device may store and use the neural network weight parameters according to a fixed-point quantization method to reduce memory and energy requirements. Data and weight parameter movement may be reduced in a processing device according to embodiments of the present invention by exploiting redundancies in and promoting reuse of both input data and requested neural network weight parameters.

In a further aspect, the present invention relates to a hearing device comprising the data processing device as described above, and further comprising a pressure detection means, for example an air pressure detection means such as a microphone, for detecting a time-varying pressure signal indicative of at least one auditory stimulus, sampling means for sampling the detected auditory stimulus to obtain an input sequence comprising a plurality of input samples, and at least one transducer for converting output sequences generated by the neural network into audible time-varying pressure signals, basilar membrane vibrations, or corresponding auditory nerve stimuli associated with the at least one auditory stimulus. An alternative or additional sensor which detects human bio-signals (e.g. EEG, otoacoustic emissions) can also be added to this device to determine or update the parameters of a hearing devices based on features derived from the time-varying bio-signals. Therefore, in some embodiments the hearing device comprises a sensor that detects human bio-signals, for example an EEG sensor.

In still another aspect, the present invention relates to a computer program comprising instructions which, when the program is executed by a computer, perform the method steps as described above. It also relates to a computer-readable medium comprising instructions which, when the program is executed by a computer, perform the method steps as described above.

In one aspect, the present invention also relates to a hearing aid or augmented hearing device based on a normal-hearing implementation or a hearing-impaired implementation according to a model as described above. Hearing impairment can be implemented using the transfer learning technique from the normal hearing implementation. The present invention also relates to a hearing aid or augmented hearing device generating electrical impulses based on the generated BM displacement values, and optionally inner-hair-cell potentials, or auditory-nerve firing patterns.

As used herein, the term "transfer-learning" refers to a technique where the weights of the neural-network-based normal-hearing cochlear model are used for the initialization of the weights of the hearing-impaired model. In some embodiments, the model is trained starting from these normal-hearing weights, and the weights are updated according to the hearing-impaired input-output pairs of the training set. This step reduces the training time significantly, by using a much smaller dataset, without significant differences in the resulting model. Apart from the cochlear stage, the same technique can be used for the implementation of hearing impairment in different stages or combinations of different hearing impairments in multiple (or all) auditory periphery stages.

The invention also relates to a computer-implemented method for emulating cochlear processing of auditory stimuli, the method comprising the steps of:
- providing a multilayer convolutional encoder-decoder neural network including
- an encoder and a decoder, together comprising at least a plurality of successive convolutional layers, for example each comprising at least one convolutional layer, preferably each comprising at least a plurality of successive convolutional layers, successive convolutional layers of the encoder having strides, for example decreasing, constant, and/or increasing strides, preferably constant and/or increasing strides, with respect to an input to the neural network to sequentially compress the input and successive convolutional layers of the decoder having strides, for example decreasing, constant, and/or increasing strides, preferably constant and/or increasing strides with respect to the compressed input from the encoder to sequentially decompress the compressed input, each of the convolutional layer comprising a plurality of convolutional filters for convolution with an input to the convolutional layer to generate a corresponding plurality of activation maps as outputs,
- at least one nonlinear unit for applying a nonlinear transformation to the activation maps generated by at least one convolutional layer of the neural network, the nonlinear transformation mimicking a level-dependent cochlear filter tuning associated with cochlear processing, for example cochlear mechanics, basilar-membrane vibration, outer-hair-cell processing, inner-hair-cell processing, or auditory-nerve processing, and combinations thereof, for example cochlear mechanics and outer hair cells,
- one or more shortcut connections, preferably a plurality of shortcut connections, between the encoder and the decoder for forwarding inputs to a convolutional layer of the encoder directly to at least one convolutional layer of the decoder,
- an input layer for receiving inputs to the neural network, and
- an output layer for generating, for each input to the neural network, N output sequences of cochlear response parameters corresponding to N emulated cochlear filters associated with N different center frequencies to span a cochlear tonotopic place-frequency map, the cochlear response parameters of each output sequence being indicative of cochlear processing, for example cochlear mechanics, for example cochlear basilar-membrane vibration and/or inner-hair-cell and/or outer-hair-cell and/or auditory nerve responses, for example a place-dependent time-varying cochlear basilar membrane vibration and/or inner-hair cell receptor potential and/or outer-hair-cell responses and/or auditory nerve fiber firing patterns, for example a place-dependent time-varying vibration of a cochlear basilar membrane,
- providing at least one input sequence of predetermined length indicative of a time-sampled auditory stimulus, and applying the at least one input sequence to the input layer of the neural network to obtain the N output sequences of cochlear response parameters, and
- optionally, summing or combining, preferably summing, the obtained N output sequences to generate a single output sequence of cochlear response parameters.

The invention also relates to a method for determining a plurality of weight parameters associated with the neural network in any one emulation method as described herein or embodiments thereof, comprising:
- providing a training dataset comprising a plurality of training input sequences, each comprising a plurality of input samples indicative of a time-sampled auditory stimulus,
- providing a biophysically accurate validation model for cochlear processing, preferably a cochlear transmission line model, a degree of accuracy of which is evaluated with respect to experimentally measured cochlear response parameters indicative of cochlear processing, for example cochlear mechanics, for example cochlear basilar-membrane vibration and/or inner-hair-cell and/or outer-hair-cell and/or auditory nerve responses, for example a place-dependent time-varying cochlear basilar membrane vibration and/or inner-hair cell receptor potential and/or outer-hair-cell responses and/or auditory nerve fiber firing patterns, for example place-dependent time-varying basilar membrane vibrations in accordance with a cochlear tonotopic place-frequency map,
- generating N training output sequences for each training input sequence, each of the N training output sequences being associated with a different center frequency of the cochlear tonotopy map,
- performing the emulation method using training input sequences to generate corresponding emulated sequences of cochlear response parameters for the neural network with respect to the same cochlear tonotopy map, and evaluating a deviation between the emulated sequences and the training output sequences arranged as training pairs, the emulated sequence and the training output sequence of each training pair being associated with a same training sequence,
- using an error backpropagation method for updating the neural network weight parameters comprising weight parameters associated with each convolutional filter,
- optionally, retraining the neural network weight parameters for a different set of neural network hyperparameters to further reduce the deviation, the different set of neural network hyperparameters including one or more of: a different nonlinear transformation applied by the at least one nonlinear unit, a different number of convolutional layers in the encoder and/or decoder, a different number of convolutional filters in any one convolutional layer of the neural network, a different length as the predetermined length for the input sequence, a different configuration of shortcut connections, or optionally a different size of the convolutional filters in any one convolutional layer of the neural network.

The invention also relates to hearing device comprising the data processing device as described herein or embodiments thereof, and further comprising:
- a pressure detection means for detecting a time-varying pressure signal indicative of at least one auditory stimulus; and/or a sensor that detects human bio-signals, for example an EEG sensor, or a pressure sensor such as an ear-canal pressure sensor,
- sampling means for sampling the detected auditory stimulus to obtain an input sequence comprising a plurality of input samples, and
- at least one transducer for converting output sequences generated by the neural network into audible time-varying pressure signals, cochlear responses; for example basilar-membrane vibrations, inner-hair-cell responses, outer-hair-cell responses, auditory-nerve responses, or corresponding auditory-nerve responses, and combinations thereof, for example basilar membrane vibrations; or corresponding auditory nerve stimuli associated with the at least one auditory stimulus.

In some embodiments, the multilayer convolutional encoder-decoder neural network comprises an encoder and a decoder, together comprising at least a plurality of successive convolutional layers, for example each comprising at least one convolutional layer, preferably each comprising at least a plurality of successive convolutional layers.

In some embodiments, the encoder has strides, for example decreasing, constant, and/or increasing strides, preferably constant and/or increasing strides.

In some embodiments, the decoder has strides, for example decreasing, constant, and/or increasing strides, preferably constant and/or increasing strides.

In some embodiments, the nonlinear transformation mimics a level-dependent cochlear filter tuning associated with cochlear processing, for example cochlear mechanics, basilar-membrane vibration, outer-hair-cell processing, inner-hair-cell processing, or auditory-nerve processing, and combinations thereof, for example cochlear mechanics and outer hair cells.

In some embodiments, the multilayer convolutional encoder-decoder neural network comprises one or more shortcut connections, preferably a plurality of shortcut connections, between the encoder and the decoder for forwarding inputs to a convolutional layer of the encoder directly to at least one convolutional layer of the decoder.

In some embodiments, the cochlear response parameters of each output sequence are indicative of cochlear processing, for example cochlear mechanics, for example cochlear basilar-membrane vibration and/or inner-hair-cell and/or outer-hair-cell and/or auditory nerve responses, for example a place-dependent time-varying cochlear basilar membrane vibration and/or inner-hair cell receptor potential and/or outer-hair-cell responses and/or auditory nerve fiber firing patterns, for example a place-dependent time-varying vibration of a cochlear basilar membrane.

In some embodiments, the method comprises the optional step of summing or combining, preferably summing, the obtained N output sequences to generate a single output sequence of cochlear response parameters.

In some embodiments, the experimentally measured cochlear response parameters are indicative of cochlear processing, for example cochlear mechanics, for example cochlear basilar-membrane vibration and/or inner-hair-cell and/or outer-hair-cell and/or auditory nerve responses, for example a place-dependent time-varying cochlear basilar membrane vibration and/or inner-hair cell receptor potential and/or outer-hair-cell responses and/or auditory nerve fiber firing patterns, for example place-dependent time-varying basilar membrane vibrations in accordance with a cochlear tonotopic place-frequency map.

In some embodiments, the different set of neural network hyperparameters include one or more of: a different nonlinear transformation applied by the at least one nonlinear unit, a different number of convolutional layers in the encoder and/or decoder, a different number of convolutional filters in any one convolutional layer of the neural network, a different length as the predetermined length for the input sequence, a different configuration of shortcut connections, or optionally a different size of the convolutional filters in any one convolutional layer of the neural network.

In some embodiments, the hearing device comprises a pressure detection means for detecting a time-varying pressure signal indicative of at least one auditory stimulus; and/or a sensor that detects human bio-signals, for example an EEG sensor, or a pressure sensor such as an ear-canal pressure sensor.

In some embodiments, the hearing device comprises at least one transducer for converting output sequences generated by the neural network into audible time-varying pressure signals, cochlear responses; for example basilar-membrane vibrations, inner-hair-cell responses, outer-hair-cell responses, auditory-nerve responses, or corresponding auditory-nerve responses, and combinations thereof, for example basilar membrane vibrations; or corresponding auditory nerve stimuli associated with the at least one auditory stimulus Particular and preferred aspects of the invention are set out in the accompanying independent and dependent claims. Features from the dependent claims may be combined with features of the independent claims and with features of other dependent claims as appropriate and not merely as explicitly set out in the claims.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, in which.

Figure 1:
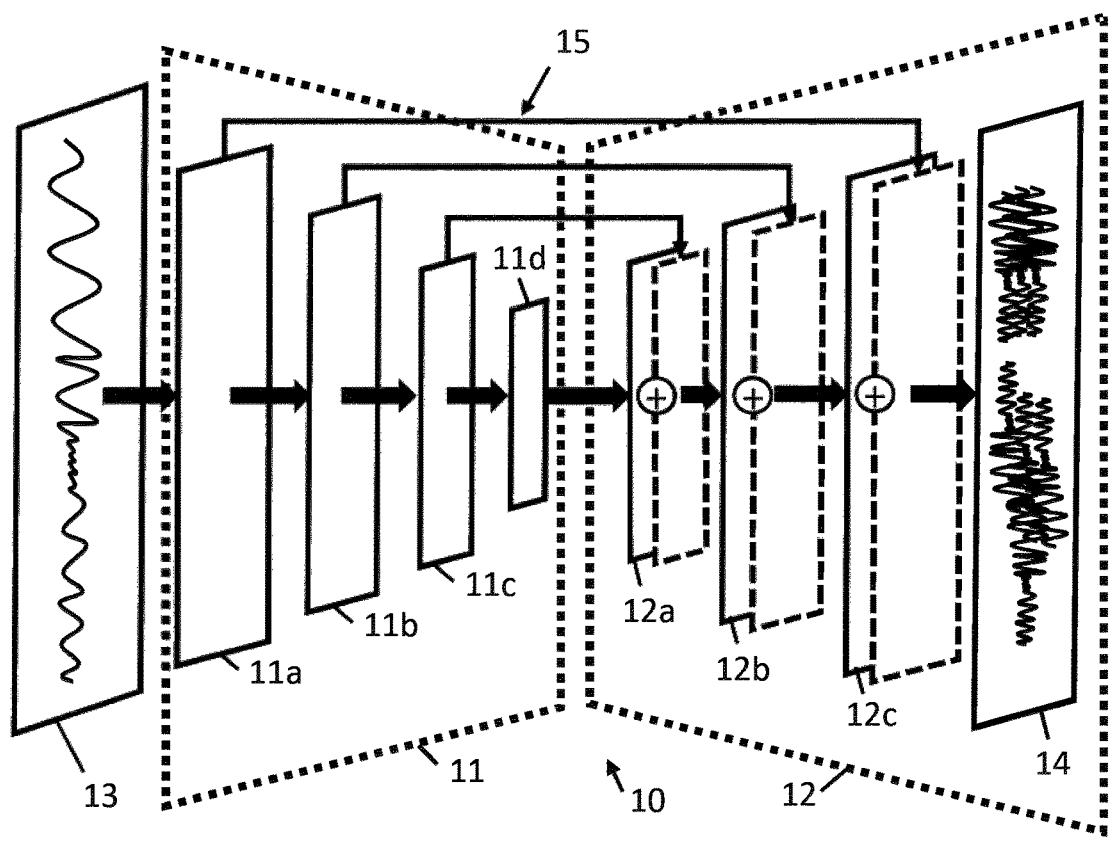
FIG. 1 shows an example of a neural network as can be used for emulating cochlear processing according to the present invention.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

Definitions

Auditory stimuli, in the context of the present invention, can be manifold and refer to acoustic signals (e.g. pressure waves) susceptible to human or animal hearing, e.g. signals comprising and conveying acoustic energy in the range from approximately 20 Hz to approximately 20 kHz for the human auditory system depending on age and health. Evidently, for non-human animals, different frequency ranges apply. As used herein, the term "cochlear processing" refers to processing of sound by the auditory periphery, and includes cochlear and neural processing of sound across various stages in the ascending auditory pathway. Cochlear processing hence refers to processing taking place in the middle ear, on the basilar-membrane (BM), within the outer- and inner-hair-cells (OHC & IHC), auditory-nerve fiber (ANF) synapses and neurons. The "CoNNear" or "cochlear model or "auditory periphery model" hence refers to an ensemble of models which each resemble the different aspects of cochlear processing. The specific elements of the CoNNear model are referred to as "BM vibration model", "IHC model", "ANF model". Each of these models will have a neural-network based described as part of the invention and will have a reference analytical description which was used for model training purposes.

Near real-time processing, live processing or close-to-live processing, in the context of the present invention, are considered in relation to the typical delays encountered in audio processing applications. Audio latency below 200 ms is generally accepted, and for live processing of audio signals delays under 20 ms are targeted.

In the context of the present invention, a neural network is considered a convolutional neural network if it comprises at least one convolutional layer. A convolutional layer comprises one or more filters, or kernels, which operate on the layer input by convolution, wherein a convolution direction is along one or several dimensions defined by an input map. In embodiments of the present invention, a convolution direction is generally one-dimensional and refers to the time dimension, or time axis, of the layer's input, which input most often is higher dimensional. Performing a convolution operation along a convolution direction generally involves multiple input dimensions or even input batches, and multiple output dimensions (filter depths), and therefore is most often carried out as a generalized tensor convolution between layer input (map) and layer filters to produce a corresponding (nonlinearly activated) layer output (map).

Successive convolutional layers of the neural network, in the context of the present invention, refer to next layers of the neural network layer stack which operate on their input map by convolution. Hence, the terminology of successive convolutional layers of the neural network includes cases of convolutional layers being immediately adjacent layers of the layer stack as well as cases in which the next convolutional layer is separated from the preceding convolutional layer in the layer stack by one or more other, non-convolutional layers. An increasing stride with respect to an input or compressed input includes a monotonic increase as well as a strictly monotonic increase.

With reference to FIG. 1, an exemplary neural network 10 used in an embodiment of the invention is now described. The neural network 10 comprises an encoder 11 and a decoder 12. Each of the encoder 11 and the decoder 12 comprise a plurality of convolutional layers, i.e. a first succession of convolutional layers 11a-d for the encoder 11 and a second succession of convolutional layers 12a-12c and 14 for the decoder 12. An input layer 13 of the neural network 10 is connected to the encoder 11 and the last convolutional layer 11d of the encoder 11 is connected to the first convolutional layer 12a of the decoder 12. The last convolutional layer 14 of the successive convolutional layers of the decoder 12 also provides the output layer of the neural network 10. The input layer 13 is adapted for receiving at least one input sequence of a predetermined length, e.g. at least one time series of sampled auditory stimuli, comprising a plurality of input samples, sampled at a predetermined sampling rate, e.g. 2048, 4096, or 8192 samples at 16 kHz or 20 kHz sampling rate corresponding to a 128 ms time window, or 1024 samples at 16 kHz sampling rate corresponding to a 64 ms time window, etc. Moreover, the input layer 13 may be adapted for receiving multiple input sequences of a predetermined length as a compounded, multi-dimensional input, e.g. three input sequences associated with three distinct unidirectional microphones. Therefore, an input to the neural network 10 has at least one time dimension and can have one or more dimensions in depth (e.g. input features). Moreover, it is possible to concatenate several inputs into a batch of inputs for processing by the neural network. Batch processing of inputs is generally supported by tensor convolutions, but the inference time is slowed down. In consequence, batch processing may be used during training where relaxed latency requirements apply and may be deactivated or disabled at runtime, e.g. in the test phase. The output layer 14 of the neural network 10 is configured for generating N distinct output sequences, N being an integer significantly larger than one, e.g. at least one hundred or more.

The successive convolutional layers 11a-d of the encoder 11 and the successive convolutional layers 12a-c and 14 of the decoder 12 each are characterized by a respective stride for which the convolution is carried out. A stride larger than one leads to a downsampling for the input to the encoder 11, e.g. the input (time) dimension between convolutional layer input map and corresponding output map is decreased by reducing an overlap in the receptive fields of the translated convolutional filters when performing a convolution operation. Therefore, successive convolutional layers 11a-d of the encoder 11 having increasing strides with respect to an input to the neural network sequentially compress the input along its direction of convolution, e.g. along the time dimension. Likewise, a stride larger than one leads to an upsampling for the compressed input to the decoder 12, e.g. the input (time) dimension between convolutional layer input map and corresponding output map is increased, e.g. by zero-padding between the layer inputs along the upsampled (time) dimension when performing a convolution operation. The convolution operations by the convolutional layers of the decoder 12 are also called transposed convolutions or (less appropriately) deconvolutions. Hence, successive convolutional layers 12a-c, 14 of the decoder 12 having increasing strides with respect to a compressed input, compressed by the encoder, e.g. the output map generated by the last layer of the encoder 11, e.g. the output map generated by the convolutional layer 11d, sequentially decompresses the compressed input. Therefore, the decoder 12 is capable of at least partially restoring compressive losses via upsampling and interpolation. For instance, the stride for each convolutional layer 11a-d of the encoder 11 in the particular embodiment in FIG. 1 may be selected as two, which leads to a cascade of power of two downsampling for the input, e.g. the strides with respect to the input to the neural network 10 are strictly monotonically increasing and given as the sequence {2; 4; 8; 16}, e.g. the compressed input comprises 16 times less input samples along the time direction as the input at the input layer 13. Similarly, the stride for each convolutional layer 12a-c, 14 of the decoder 12 in the particular embodiment in FIG. 1 may also be selected as two, thereby yielding a cascade of power of two upsampling for the compressed input, e.g. the strides with respect to the compressed input generated by the encoder 11 are strictly monotonically increasing and given as the sequence {2; 4; 8; 16}, e.g. the generated output sequences by the last convolutional layer 14 of the decoder comprises 16 times more samples along the time direction as the compressed input presented to the first convolutional layer 12a of the decoder. In this particular example, the number of input samples in the input sequence(s) is matching the number of output samples in each generated output sequence. However, there are alternative embodiments for which there may be more output samples generated in each output sequence than there are input samples in each input sequence, e.g. in embodiments for which an input sampling rate is two times slower than an output sampling rate. To achieve this, such embodiment may comprise three convolutional layers in the encoder and three convolutional layers in the decoder with stride sequences {2; 8; 8} and {2; 8; 64} with respect to the input and compressed input, respectively. It is observed that in this particular case, the stride sequence is not increasing as a power of two, but even faster. It is also noted that the increase of the stride sequence for the encoder is not strictly monotonic, but only monotonic, because the last convolutional layer of the encoder has been selected to have an absolute stride of one.

Overall, the neural network 10 thus represents a multilayered convolutional neural network with an encoder-decoder architecture, for which the multiple layers lead to a mutual coupling of emulated cochlear filters, in this example cochlear BM filters. It is an advantage of the encoder-decoder architecture that the feature space for the compressed input has a relatively small dimensional size, e.g. a number of compressed (encoded) features is small, which makes the overall neural network less vulnerable to overfitting and more robust against external variations that are not controlled, e.g. speaker variations. More specifically, each speaker has an individual accent, fundamental frequency, and speaking speed which should not affect the underlying trained neural network model for cochlear processing (i.e. the architecture, including the learnt neural network weights), much the same as the human auditory system does not physiologically depend on or is influenced by these speaker variations. It is important to note that this speaker-invariant behavior of the neural network model does not mean that the speaker variations are not recovered at the neural network output layer, e.g. the processed data reflects such variations, but the neural network architecture does (almost) not.

For the exemplary embodiment in FIG. 1 for cochlear BM processing, each convolutional layer comprises a number of distinct convolutional filters acting on the layer input by (tensor) convolution, e.g. each of the convolutional layers 11a-d of the encoder 11 and the convolutional layers 12a-c of the decoder 12 comprise 128 distinct convolutional filters (or kernels), and their respective receptive fields are set to a length of 64 samples along the time dimension of the layer input. For the last convolutional layer 14 of the decoder, here the output layer of the neural network 10, the receptive field for the filters are also set to 64, but the number of distinct filters in this layer, i.e. the filter depth, was chosen to be 201 corresponding to 201 different center frequencies of a cochlear tonotopic place-frequency map, e.g. 201 center frequencies spanning the frequency range from 100 Hz to 12 kHz of the Greenwood tonotopy map. The filter depth and receptive field of filters of a convolutional layer are not limited to the example values above and may be varied depending on the cochlear processing stage, application, required accuracy of emulation, frequency span and resolution of the tonotopy map, etc. There are approximately 11.3 million trained neural network parameters associated with the neural network 10 in FIG. 1, which comprises a total of eight convolutional layers. It was found during training of the neural network that smaller receptive fields, e.g. below 64 samples, led to a pronounced reduction of cochlear dispersion (cochlear response delay, e.g. determined in milliseconds, between low frequency and high frequency components, see FIG. 5) in the observed output sequences, whereas larger receptive fields only modestly contributed to an improved cochlear dispersion, which may be rejected on the grounds of a significant increase in neural network weights associated with these larger receptive fields.

For the successive stages of cochlear processing (IHC and AN), the respective layers forming their architectures can retain the same number of distinct filters (i.e. filter depth, here chosen to be 201) as the last layer of the BM stage has, so that the IHC and AN processing can be applied to the same center frequencies of the cochlear tonotopic place-frequency map, e.g. 201 center frequencies spanning the frequency range from 100 Hz to 12 kHz of the Greenwood tonotopy map.

The neural network also comprises at least one nonlinear unit for nonlinearly transforming an activation map generated by one of the convolutional layers of the neural network to generate a corresponding output map. The nonlinearity is preferably applied element-wise and mimics a level-dependent, symmetric cochlear filter tuning associated with cochlear outer hair cells, e.g. compressive nonlinearity in the outer-hair-cell motor action on the basilar membrane vibrations. A preferred nonlinearity by the nonlinear unit is given as the element-wise applied hyperbolic tangent ("tanh") activation function for nonlinearly transforming the activation map entries of a convolutional layer into the corresponding sample of the layer output map. For the particular neural network 10 in FIG. 1, a plurality of nonlinear units is provided. More specifically, the activation maps generated by each convolutional layer 11a-d, 12a-c, 14 of the encoder 11 and the decoder 12 are nonlinearly transformed by applying the tanh activation function element-wise. However, embodiments of the invention are not limited to solely nonlinearly transformed convolutional layers and there may be one or more linearly activated convolutional layers present in the neural network. Furthermore, the nonlinearity is not limited to an element-wise applied hyperbolic tangent. Other choices may command themselves to the skilled person in the field, for example a squashing function applied vector-wise to vectors of the convolution layer activation map, e.g. the vectors formed by all filter responses for each convolution step, or an element-wise applied, parametric nonlinearity of the form $\alpha*\tanh(x)+(1-\alpha)\,\text{sign}(x)$ with layer-dependent $\alpha$ varying between zero and one.

For each stage, the activation functions are preferably chosen based on biophysical properties. Therefore, in some embodiments, different stages have different nonlinear activation functions. Similarly, in some embodiments, the activation functions differ between the encoder and the decoder. For example, a tanh activation may be used in the layers of the encoder, while a sigmoid activation function may be used in the layers of the decoder.

In general, the properties of the neural networks may be different for each stage, including the length of the input sequence, the number of layers, the number of filters in each layer, the activation function, and consequently also the total number of parameters.

A plurality of shortcut connections 15 are also included in the neural network 10. They provide connections between convolutional layers 11a-c of the encoder 11 and convolutional layers 12b-c and 14 of the decoder 12. More specifically, the shortcut connections 15 are arranged for simultaneously forwarding an input to a convolutional layer of the decoder when this input is applied to a convolutional layer of the encoder 11 having shortcut connections. This means that one or more convolutional layers of the multilayered neural network 10 are effectively bypassed or skipped for this forwarded input. It is noted that the receiving convolutional layer of the decode is not processing these additional forwarded inputs until the regular inputs are also available, e.g. the inputs which are the result of the sequential processing by the different intermediate layers of the multilayered neural network that were effectively bypassed. In literature, shortcut connections are also referred to as residual connections, lateral connections or skip connections. For the particular embodiment in FIG. 1, there are shortcut connections 15 for connecting inputs to the first encoder convolutional layer 11a to the fourth decoder convolutional layer 14, the inputs to the second encoder convolutional layer 11b to the third decoder convolutional layer 12c, and inputs to the third encoder convolutional layer 11c to the second decoder convolutional layer 12b. In other embodiments, however, more or less shortcut connections may be provided between the convolutional layers of the encoder 11 and the decoder 12. The shortcut connections 15 ensure the temporal alignment between input sequence and generated output sequences, e.g. by ensuring temporal alignment also between convolutional layers of the encoder 11 and convolutional layers of the decoder 12, e.g. between each of the convolutional layers 11a-c of the encoder 11 and a corresponding one convolutional layer 12b-c and 14 of the decoder 12, wherein the correspondence is established by the matching of at least the layer input dimension associated with time. In consequence, the temporal phase information that is lost during input compression by the encoder 11 is recovered by the decoder 12 during decompression. In addition to the characteristic top-down and subsequent bottom-up approach in the encoder-decoder architecture, the shortcut connections between convolutional layers of the encoder and decoder provide an additional input to the convolutional layers of the decoder during output generation and refinement. In particular, the repeated downsampling in the encoder generates a plurality of features extracted at multiple scales, which are then used, via the shortcut connections, as additional inputs for the decoder. Therefore, embodiments of the present invention also provide multiscale filtering, similar to what is achieved by wavelet filter banks, for example.

Various types of shortcut connections are available for selection by the skilled person in the field. The simplest and most economic type of shortcut connections, e.g. in terms of number of added neural network weights, training and inference energetic costing, are weight one or unitary, untrained connections. More sophisticated types are also possible, e.g. with the goal of increasing the overall accuracy of the neural network or of learning input pattern dependent forwarding of inferred features at multiple scales in the encoder, which types include, without being limited thereto, gated shortcut connections as used in highway networks, for instance, or scaled/weighted shortcut connections. In this respect, a weighting matrix for scaled shortcut connections may be a sparse matrix, which advantageously leads to fewer implemented shortcut connections and a potential increase of the neural network's overall robustness against noise.

Emulating cochlear processing will reproduce the basilar membrane vibrations excited by externally applied noise, but enhanced cochlear processing with noise removal, which is based on the emulation of cochlear processing, may be obtained in particular embodiments of the invention too. Regardless of the external noise sources affecting the auditory stimulus, also internal noise sources may have a negative impact. For example, the addition of quantization noise as a result of a sampling method for obtaining a time-sampled input sequence indicative of the auditory stimulus may constitute an internal noise source. Therefore, noise robustness of the neural network can be a quantity of interest for hearing quality assessments.

It follows from the foregoing arguments that the combination (the "+" sign in FIG. 1) of forwarded inputs and regular inputs may be performed differently for each convolutional layer of the decoder receiving those. Preferred combinations, because energetically cheap, of forwarded and regular inputs to any one convolutional layer of the decoder are provided as an element-wise summing or averaging thereof. However, more advanced types of shortcut connections may provide an element-wise nonlinearity applied to a weighted sum of regular and forwarded inputs to control a relative contribution of the regular and the forwarded input, respectively.

The output layer 14 of the neural network 10 is adapted for generating, for each input to the neural network, N output sequences of cochlear response parameters corresponding to N emulated cochlear filters, for example BM filters, IHC, ANF responses, associated with N different center frequencies to span a cochlear tonotopic place-frequency map, wherein the cochlear response parameters of each output sequence are indicative of a place-dependent time-varying cochlear BM vibration, IHC receptor potential, or ANF firing patterns, for example a place-dependent time-varying vibration of a cochlear basilar membrane. When practicing embodiments of the present invention, the skilled person may select one of the following, known maps as cochlear tonotopic place-frequency maps or scales: equivalent rectangular bandwidth (ERB) scale spacing, Greenwood map, Bark scale, etc. This list is not exhaustive and other suitable cochlear tonotopic place-frequency maps may come to skilled person's attention. The place-dependent time-varying vibration of a cochlear basilar membrane may be indicated in terms of local membrane displacements, local membrane velocities, local membrane accelerations, local pressure or acceleration forces on the membrane, or combinations thereof.

Embodiments of the present invention are not limited to neural networks comprising only convolutional layers, although they are preferable in view of their weight sharing and shift invariance, e.g. invariance to the absolute moment in time an auditory stimulus occurs, e.g. a click sound. Sharing a number of weights in a layer-to-layer mapping is saving memory and computation requirements and allows for an efficient hardware implementation on dedicated accelerator chips. Therefore, increasing the number of network layers that can be implemented as a convolution operation is a favorable choice when low-energy efficient hardware implementations of the computer-implemented method are sought, e.g. in hearing devices and ear-worn hearing aids comprising a battery. Other layers which may form part of the neural network include dense layers, fully connected layers, pooling layers, etc., and are present in other embodiments described further below. The other layers, if present, may be arranged between the input layer and the encoder, between the encoder and the decoder, between the decoder and the output layer, and, more generally, between successive convolutional layers of the encoder and/or decoder without impact on the sequence of convolutional layers, i.e. two successive convolutional layers remain successive, regardless of one or more non-convolutional layers being inserted.

During operating conditions, the neural network typically may receive at least one input sequence that is applied to its input layer 13. The input sequence is indicative of an auditory stimulus, e.g. a pure tone, a click sound, speech, etc. For instance, a single input sequence may in one example comprise 2048 samples of a speech signal which has been sampled at 16 kHz in the time domain. Sampling rates can be higher than 16 kHz, e.g. 20 kHz, 32 kHz or 44 kHz, or higher. Then the applied input sequence is fed from the input layer 13 to the first layer of the encoder 11, e.g. to the first convolutional layer 11a. The activation map generated by the first layer of the encoder 11 is passed on to the next layer directly or the nonlinear unit first to apply a nonlinear transformation. This is repeated for each layer of the encoder 11 to obtain a compressed input as output map generated by the last layer of the encoder. Next, the decoder 12 receives the compressed input form the encoder 11 at its first layer, e.g. the first convolutional layer 12a of the decoder 12. The activation map generated by the first layer of the decoder 12 is passed on to the next layer directly or the nonlinear unit first to apply a nonlinear transformation. At least one layer of the decoder 12 is receiving an output map of a layer of the encoder 11 as additional input via a plurality of shortcut connections 15. This additional input is combined with the regular sequential input from the preceding layer, e.g. by summation or averaging, to produce the input map to this layer of the decoder 12. The foregoing steps are repeated for each layer of the decoder 12 to obtain a decompressed input as output map generated by the last layer of the decoder 12. This last layer of the decoder may be the output layer 14. Eventually, the output layer generates N output sequences which each comprise a plurality of samples in the time domain. These output samples in the time domain are associated with cochlear responses (e.g. BM vibration, IHC receptor potential, ANF firing), for example basilar membrane vibrations.

For example, the first convolutional layer 11a is a layer that performs a strided and padded convolution (stride parameter two, 'same' padding) between the input sequence and each one of 128 one-dimensional convolutional filters of filter length 64 to generate a corresponding activation map of depth 128 and length 1024 (optionally 2048, 4096, or 8182). This activation map is then nonlinearly transformed into an output map for the first convolutional layer 11a, e.g. via an element-wise applied hyperbolic tangent. This first output map is then used as input map for the next layer of the encoder, e.g. the second convolutional layer 11b, and the strided convolution and nonlinear transformation are again performed for this second convolutional layer 11b, and so on. In an embodiment of the invention as shown in FIG. 1, each convolutional layer of the encoder 11 may have a stride parameter of two and a depth of 128 such that the last, nonlinearly transformed activation map generated by the last convolutional layer 12d is characterized by a depth of 128 and a compressed length (along the time dimension) of 128 samples. The sequence of convolutional layers 12a-c, 14 of the decoder 12 then re-expand this compressed length/time dimension, e.g. it decompresses the compressed input from the encoder 11, by performing repeated strided transposed convolutions, e.g. convolutions of stride two and padding for upsampling and interpolation. In consequence, the length/time dimension of the output map generated by the last convolutional layer 14 of the decoder, e.g. the output layer 14 of the neural network 10, comprises again 2048 samples. The output layer 14 differs however from the other convolutional layers 12a-c of the decoder 12 in that the depth is set to the number N of distinct center frequencies of a tonotopic map, e.g. N=201 center frequencies according to the Greenwood map. In the particular example in FIG. 1, the second convolutional layer 12b of the decoder 12 receives, via shortcut connections 15, the output map generated by the third convolutional layer 11c of the encoder 11 as additional input, in addition to the regular input which corresponds to the output map generated by the first convolutional layer 12a of the decoder 12. The two inputs are combined into a single input having same dimensions, e.g. by summing or averaging the additional input and the regular input to layer 12b. Likewise, the third convolutional layer 12c of the decoder 12 receives, via shortcut connections 15, the output map generated by the second convolutional layer 11b of the encoder 11 as additional input, in addition to the regular input which corresponds to the output map generated by the second convolutional layer 12b of the decoder 12, and the two inputs are combined into a single input having same dimensions, e.g. by summing or averaging the additional input and the regular input to layer 12c. Also, the fourth and last convolutional layer 14 of the decoder 12 receives, via shortcut connections 15, the output map generated by the first convolutional layer 11a of the encoder 11 as additional input, in addition to the regular input which corresponds to the output map generated by the third convolutional layer 12c of the decoder 12, and the two inputs are combined into a single input having same dimensions, e.g. by summing or averaging the additional input and the regular input to layer 14.

In a variation, the at least one input sequence comprises a pre-context and/or a post-context portion, e.g. a plurality of samples in the time domain that precede or succeed the sampled signal portion of interest, e.g. the center portion of the input sequence between pre-context and post-context portion comprising the samples indicative of the auditory stimulus of interest. The pre-context and/or post-context portions may be obtained by applying a sliding sampling window with overlap regions to the acquired and sampled audio signal, e.g. they may correspond to 256 additional samples each, appended to the left and the right of a 2048 sample long portion of interest, e.g. the input sequence may comprise a total of 2048+2*256=2560 samples. It is an advantage of the pre-context and/or post-context portions to avoid discontinuous behavior near the end portions of each input sequence as well as artifacts in the generated output sequences. Such discontinuous behavior, e.g. due to the sharp edge of the sliding sampling window and zero padding, introduces artificial high frequency content into the emulated cochlear processing that would be absent in the continuous cochlear processing of the auditory system. These spurious fast on/off transitions decay within the pre-context and/or post-context portions during processing by the neural network and do not influence the center portion of interest. In such embodiments, the output sequences generated by the output layer of the neural network may be cropped to the center portion of interest, which is free of artifacts, for further processing, e.g. the appended samples to the left and/or right of the center portion may be removed (as the last layer in the decoder model).

Figure 8:
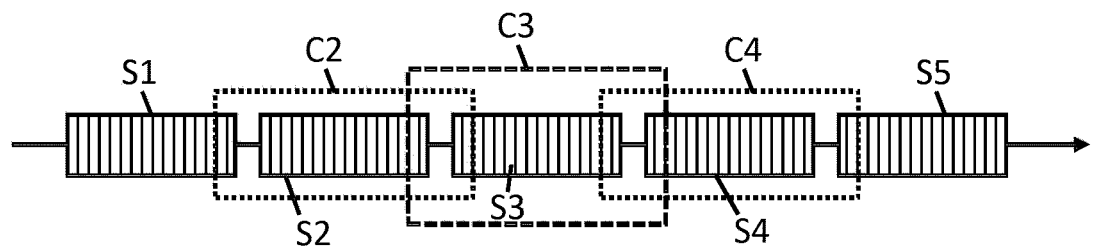
FIG. 8 illustrates a sampling operation for input sequences with context information in accordance with some embodiments of the present invention.

In FIG. 8, the sampling action of a sliding window with overlap regions is illustrated and can be used in embodiments of the present invention that include the pre-context and post-context portions. The consecutive sampled signal portions (frames) of interest are indicated as sequences S1 to S5 (the gaps between adjacent portions are only drawn for better visibility). A sampling window (C2 to C4) of length larger than the length of each sequence S1 to S5 is sliding along the horizontal time axis and is consecutively aligned at the center positions of adjacent sequences. Being larger than the sequence on which the sliding window is aligned, also samples of the two neighboring sequences are sampled. For instance, the sampling window C3 is positioned and centered on the third sequence S3 and overlaps with samples of both the second and the fourth sequence S2, S4. These overlap samples are providing the additional context information.

The context portions are optional and may not be required for sufficiently long input sequences or may be absent in applications for which a less accurate emulated cochlear processing can be afforded, for example in speech recognition applications using the neural network as pre-processor before analyzing and classifying phonemes.

Figure 5:
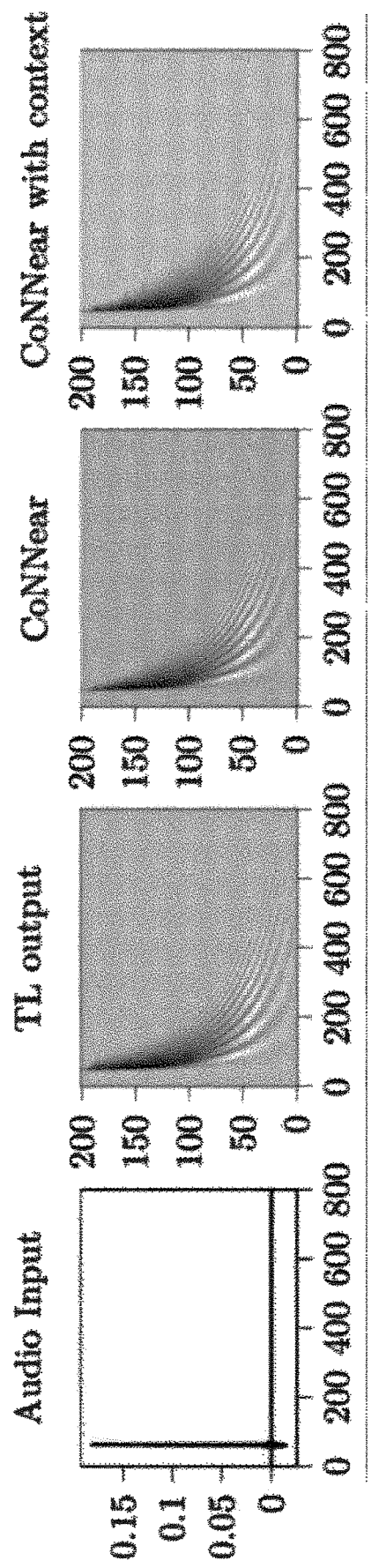
FIG. 5 shows, from left to right, an impulse-like excitation used as auditory stimulus and the corresponding output sequences, arranged as 2D maps, of a transmission line model for emulating BM processing, of a neural network for emulating BM processing as shown in FIG. 1, and of neural network for emulating BM processing as shown in FIG. 1 but with extended context.

FIG. 5 shows, respectively, the output sequences generated by a 1D transmission line model for cochlear BM processing (second from the left), a neural network emulating cochlear BM processing as described with respect to FIG. 1 (third from the left), and a neural network emulating cochlear processing as described with respect to FIG. 1 and additionally using past and future input context (at the right), which output sequences are generated in response to an impulse-like excitation used as auditory stimulus shown at the left, e.g. a short click sound typically used in physiological studies. The output sequences are arranged as 2D maps with the axis of time samples, sampled at a sampling rate of 20 kHz, as horizontal axis and the axis of distinct place-dependent center frequency channels (e.g. selected according to the Greenwood map with N=201 channels) as the vertical axis. This 2D map of generated output sequences is very useful for assessing cochlear dispersion. For instance, it can be derived from the 2D maps in FIG. 5 that the dominant part of cochlear dispersion is comprised in a time interval which lasts about 12 ms (e.g. up to time sample 200 approximately). This is an indicator for the delay experienced during human cochlear processing. FIG. 5 also demonstrates that the neural networks for emulating cochlear processing reproduce in a very detailed and faithful way the response of a transmission line model as reference model.

Figure 6:
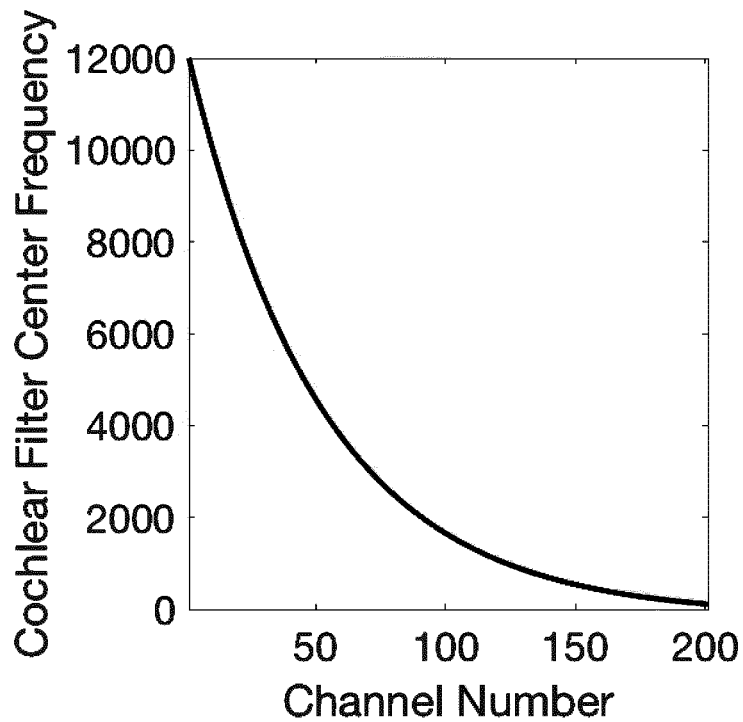
FIG. 6 illustrates the relationship between place-dependent center frequency and channel number according to the Greenwood map and N=201, as can be used for embodiments in accordance with the present invention.

FIG. 6 illustrates the relationship between center frequencies and channel number according to the Greenwood map and N=201, as used for obtaining the output maps in FIG. 5 above.

Figure 9:
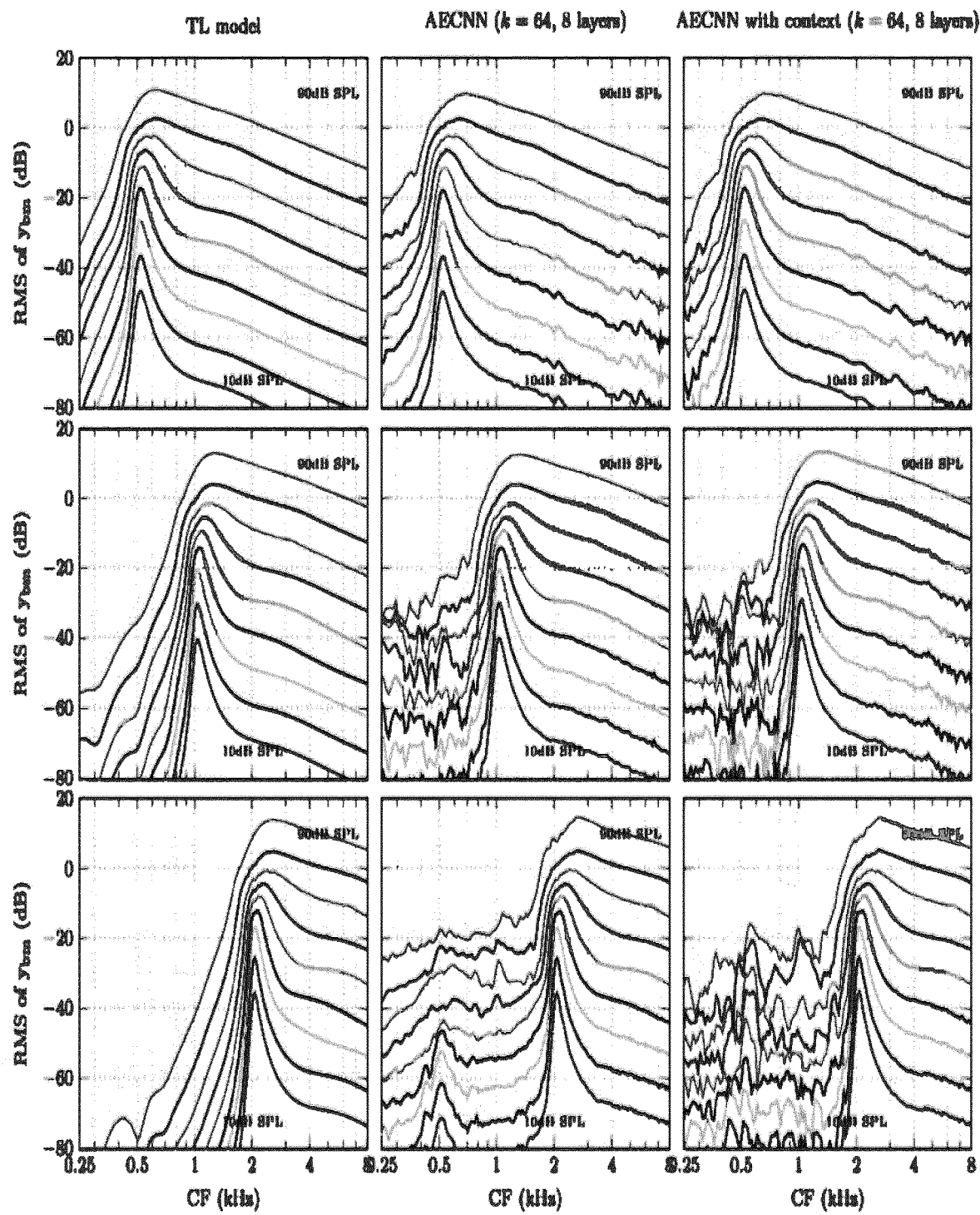
FIG. 9 shows, from left to right, output sequences of a transmission line model for emulating cochlear BM processing, of a neural network for emulating cochlear BM processing as shown in FIG. 1, and of neural network as shown in FIG. 1 but with extended context, generated in response to three different pure-tone excitations at various levels, used as auditory stimulus. For each simulated CF, the root-mean-square level of the BM response for stimuli with levels between 10 and 90 dB SPL was calculated.

Good agreement between the output sequences generated by an accurate transmission line model for cochlear BM processing and by neural networks for emulating cochlear BM processing is also observed in FIG. 9. This figure was obtained for acoustic pure-tone stimuli at various acoustic pressure levels, e.g. three different pure-tone frequencies in each column with acoustic pressure levels ranging between 10 dB SPL and 90 dB SPL. The generated output sequences being periodic for pure-tone excitations, only the root mean square energy of the emulated, basilar membrane vibration (y_rms) has been reported (vertical axis) for each place-dependent center frequency (CF) of the tonotopic map (horizontal axis). The transmission line (TL) response curves are shown in the left column as reference curves, for which there is a good agreement with the corresponding response curves obtained for the neural networks for emulating cochlear BM processing with (right column) and without (middle column) input context. Besides, the frequency selectivity as well as shapes and coupling of cochlear BM filters emulated by neural network models of cochlear BM processing are faithfully reproduced, e.g. a pronounced filter resonance peak is obtained at the frequency of the pure-tone stimulus. A shoulder at the high-frequency side of the peak indicates the coupling of filters (the higher frequencies are exited at the stiffer part of the basilar membrane closer to the oval window). It is also visible in FIG. 9 that the frequency-selective behavior (e.g. gain, tuning) diminishes for higher excitation levels in a nonlinear way.

A neural network according to embodiments of the invention can be trained with training data obtained from a validation model for cochlear processing that is biophysically accurate, e.g. the reference output sequences generated by the validation model are used as training targets. An accurate validation model is preferably provided as a time-domain transmission-line model for the cochlea and BM vibrations in particular. Analytical reference IHC and ANF transduction models should be as biophysically realistic as possible, and are preferably used in connection with cochlear transmission line models for training and evaluation purposes.

When the cochlea is stimulated, the resulting basilar membrane vibrations (e.g. displacement and velocity) are quantities which vary continuously in space along the BM and in time. For simulation or modelling purposes it is common to first discretize the basilar membrane in space, i.e. to model its vibration as a discretized version of a one-dimensional, non-uniform transmission line. This results in an array of coupled, nonlinear oscillators that are also subject to delayed feedback. A solution to the equation of motion for the set of coupled oscillators can be obtained through numerical integration for the time variable, wherein ensuring stability conditions is paramount. The more specific details and selections of relevant model parameters, such as basilar membrane width/height, stiffness, cochlear fluid density, middle ear resistance, etc., are described, for example, in Verhulst, Sarah et al. "Nonlinear time-domain cochlear model for transient stimulation and human otoacoustic emission", The Journal of the Acoustical Society of America vol. 132, 6 (2012), Altoè, Alessandro et al. "Transmission line cochlear models: Improved accuracy and efficiency", The Journal of the Acoustical Society of America vol. 136, 4 (2014). Verhulst, Sarah et al. "Functional modeling of the human auditory brainstem response to broadband stimulation", The Journal of the Acoustical Society of America, vol. 138 (2015), and, Verhulst, Sarah et al. "Computational modeling of the human auditory periphery: auditory-nerve responses, evoked potentials and hearing loss", Hearing Research, vol. 360 (2018). Other and more general approaches to time-domain biophysical models of the cochlea may also serve as validation model, for instance, Allen, Jont B. "Cochlear micromechanics—a physical model of transduction." The Journal of the Acoustical Society of America68.6 (1980): 1660-1670, Sisto, Renata, et al. "Different models of the active cochlea, and how to implement them in the state-space formalism." *The Journal of the Acoustical Society of America* 128.3 (2010): 1191-1202, or Meaud, J., and Lemons, C. (2015). "A physiologically-based time domain model of the mammalian ear," in Mechanics of Hearing: Protein to Perception, edited by D. Karavitaki and D. Corey, Proceedings of the 12th International Workshop on the Mechanics of Hearing (American Institute of Physics, Melville, N.Y.), Vol. 1703, No. 1, p. 070009. Validation models used in accordance with embodiments of the present invention do not have to be purely time domain models, but may also include frequency-domain models which provide a (cascaded) parallel filters combined with a time-to-frequency and a frequency-to-time transform for converting time-domain input sequences into a frequency presentation (e.g. spectrograms) and vice versa, e.g. Fourier transform, fast Fourier transform, z-transform.

The transmission line model are in general biophysically very accurate since the model parameters can be optimized to fit or, in addition or alternatively thereto, be selected from physiological measurements of the inner ear stimulated by sound. The accuracy of the transmission line models is reflected by their capability to faithfully reproduce characteristic cochlear phenomena such as, but not limited to, longitudinal coupling of cochlear BM filters or cascaded filtering, otoacoustic emissions, distortion products, compressive nonlinearity, frequency dispersion and group delays, (place-dependent) frequency selectivity.

Notwithstanding their usefulness, a disadvantage of these transmission line models is their computational complexity, which limits their applicability in live or real-time audio processing. Solving the system of coupled differential equations with a satisfactory level of accuracy is a matter of seconds of computation time. Such high latency and the energy cost involved in finding a solution trajectory within this complex model are factors that preclude an efficient model implementation in digital signal processors of hearing aids or ear-worn hearing devices.

A backpropagation algorithm typically may be used to train and update the neural network weights, e.g. a backpropagation algorithm using conjugate gradient or stochastic gradient updates and a fixed or adaptive learning rate. Input sequence for training may be taken from an available speech corpus. During the training phase or training passes, deviations between the output sequences generated by the validation model and the neural network are repeatedly evaluated under an error metric, for example the L1-norm, from which gradient information for updates with respect to the neural network weights is derived. The training passes may use single input sample sequences or mini-batches formed thereof. A stopping criterion, when fulfilled, indicates that neural network has been trained sufficiently, e.g. below a particular residual loss.

For instance, a neural network in accordance with embodiments of the present invention may be trained using the TIM IT speech corpus for the input training sequences. The training targets are determined as the N output sequences generated by a transmission line model as described by Verhulst, Sarah et al. "Nonlinear time-domain cochlear model for transient stimulation and human otoacoustic emission", The Journal of the Acoustical Society of America vol. 132, 6 (2012) and Verhulst, Sarah et al. "Computational modeling of the human auditory periphery: auditory-nerve responses, evoked potentials and hearing loss", Hearing Research, vol. 360 (2018). A backpropagation algorithm using mini-batches of size 64, the Adam optimizer and a learning rate of 1e-4 can suitably update and train the neural network weight parameters. An L1-loss error metric may be monitored during successive training epochs (e.g. up to 60 training epochs) and stopped as soon as the change in the L1-loss decreases below a threshold parameter, e.g. relative change in the L1-loss below 0, 1 for at least five successive epochs. Different neural network architectures and associated hyperparameters such as number of convolutional layers in the encoder and decoder, respectively, the length of the input sequences, the number of center frequencies N, the number and receptive field size of convolutional filters in each layer, the nonlinearity applied by the nonlinear unit, the topology of the skip connections, the layer strides, etc., can then be evaluated under a validation data set and their performances compared to each other, e.g. to select the best performing one. Preferably, the validation data set comprises a set of auditory stimuli that are commonly used in the auditory modeling and research field, e.g. tone and click stimuli are frequently used to describe the characteristics of different aspects or physiological elements in cochlear processing. Of course, these stimuli were not present in the training set. It has been verified under validation testing that all important aspects of human cochlear mechanics have been accurately been captured by the trained neural network, including aspects such as frequency selectivity, level-dependent tuning and compression, cochlear dispersion, cochlear distortion products and cochlear step responses.

It is an advantage of embodiments of the present invention that trained neural networks can be quickly adjusted, requiring only few further training samples, to reflect changes in the cochlear processing, e.g. the important changes related to hearing impairments. A modified validation model may be provided for this purpose, e.g. a biophysically accurate transmission line model capturing and modelling the hearing impairment, e.g. based on known effects or measured individual audiograms, otoacoustic emissions (OAEs), or auditory evoked potentials (AEPs). This is beneficial to people wearing hearing aids as hearing-damage parameters derived from measured audiograms or auditory evoked potentials can easily be used to train an individualized neural network model which can be implemented on a processing device of the hearing aid. The adjustments may be carried out off-line, e.g. on an external computer, and the adjusted neural network weight parameters are transmitted and stored on a memory device of the hearing aid the processing devices can access, or the adjustments are carried out online, e.g. directly by the processing device of the hearing aid. In variations, rather than adjusting the trained neural network weight parameters by retaining, an extension module of the neural network may become active and be trained taking the modified validation model or a combination of modified and the original (normal), unmodified validation model into account.

Fast retraining or fast training of extensions to the trained neural network can also benefit the accuracy improvements in large, deep convolutional neural networks for speech recognition applications, in which the neural network for emulating cochlear processing is used as a pre-processing module. Web-based or cloud-based server applications may collect new speech samples, or auditory evoked potentials, in real-time, hourly, or daily, and use it for continuously readjusting the neural network weight parameters.

Figure 14:
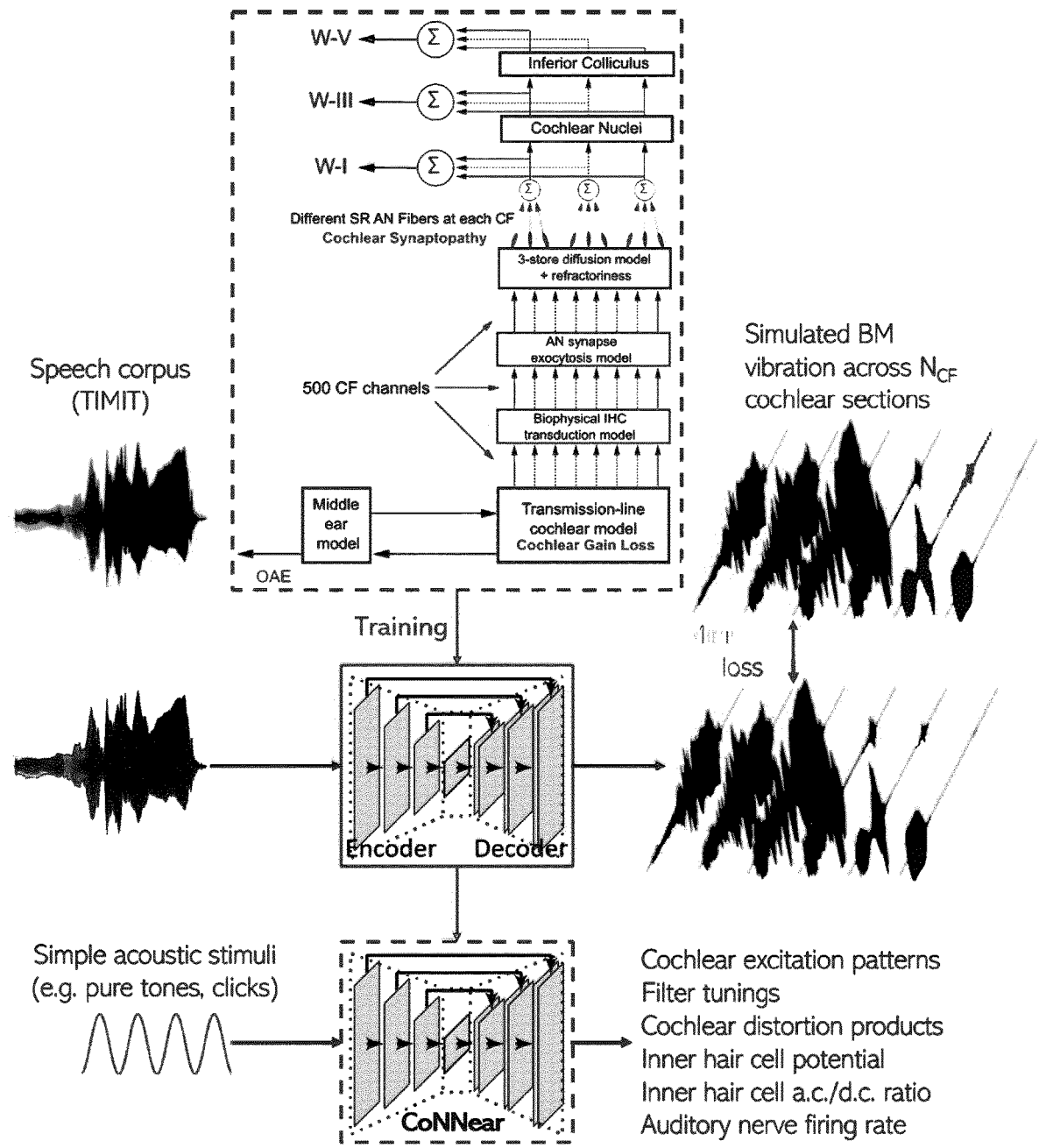
FIG. 14 illustrates the approach to extract, approximate, train and evaluate the outputs of the different stages of the auditory periphery model. The top dashed box shows all the elements included in a TL-based cochlear model which includes analytical descriptions of middle-ear, cochlear BM vibration, inner-hair-cell, auditory nerve, and cochlear nucleus, inferior colliculus processing. Simulated TL-model outputs of the above named processing stages (either for all simulated CFs or as a sum over a number of CFs) can be used to train different processing stages of the CoNNear model. An example is shown here where the TL-model BM vibration outputs to a speech corpus are used to train the BM vibration CoNNear model. In the example the L1 loss between simulated CoNNear and TL-model outputs is used to determine the CoNNear parameters. After training, the performance of the resulting CoNNear model is tested using basic acoustic stimuli which are often used in auditory neuroscience and hearing research (e.g. see the simulations in FIGS. 5, 9, 11, 12).

FIG. 14 shows an example of the model training and evaluation steps with applications to simulating cochlear BM vibrations. Simulations of a reference TL-model of cochlear processing (top gray dashed box) to a speech corpus are used to define and optimize the parameters of the neural-network of cochlear BM vibration. Performance of the trained neural-network model (e.g. FIG. 5 and FIG. 9) is conducted using simple acoustic stimuli which were not used during the model training phase by comparing the responses of the neural-network model to those of the reference TL-model which was used for training.

Figure 15:
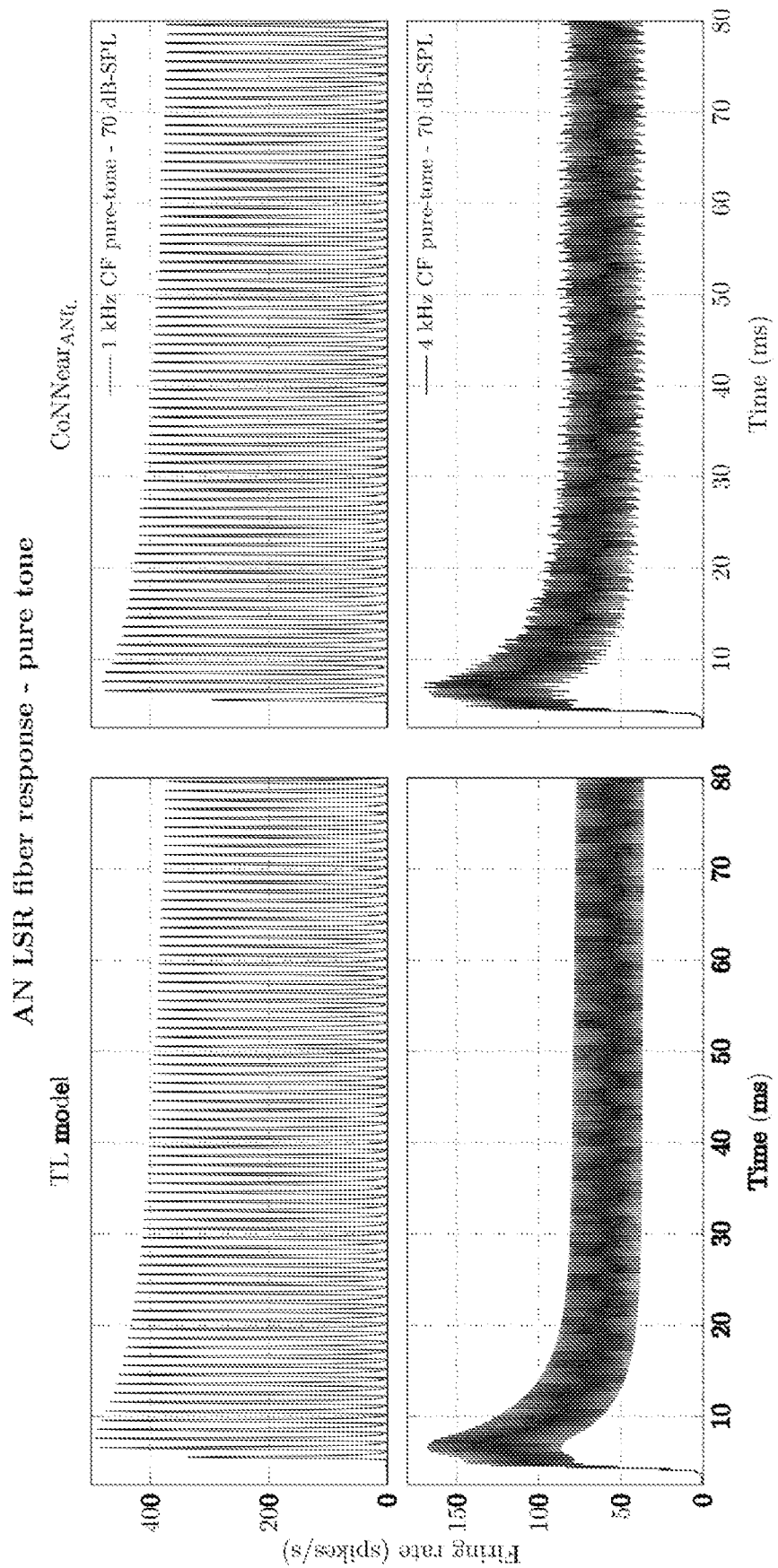
FIG. 15 shows the responses of an embodiment of this invention which simulates the cochlear ANF responses (instantaneous firing rates) for a low-spontaneous rate ANF.

FIG. 15 shows the responses of an embodiment of this invention which simulates the cochlear ANF responses (instantaneous firing rates) for a low-spontaneous rate ANF. Reference TL model simulations which were used for training are shown on the left and the CoNNear responses are shown on the right. Responses are shown in response to an acoustic pure-tone of 1 or 4 kHz. Aside from some low-level NN-noise, the CoNNear ANF model accurately captures the reference simulations.

Figure 16:
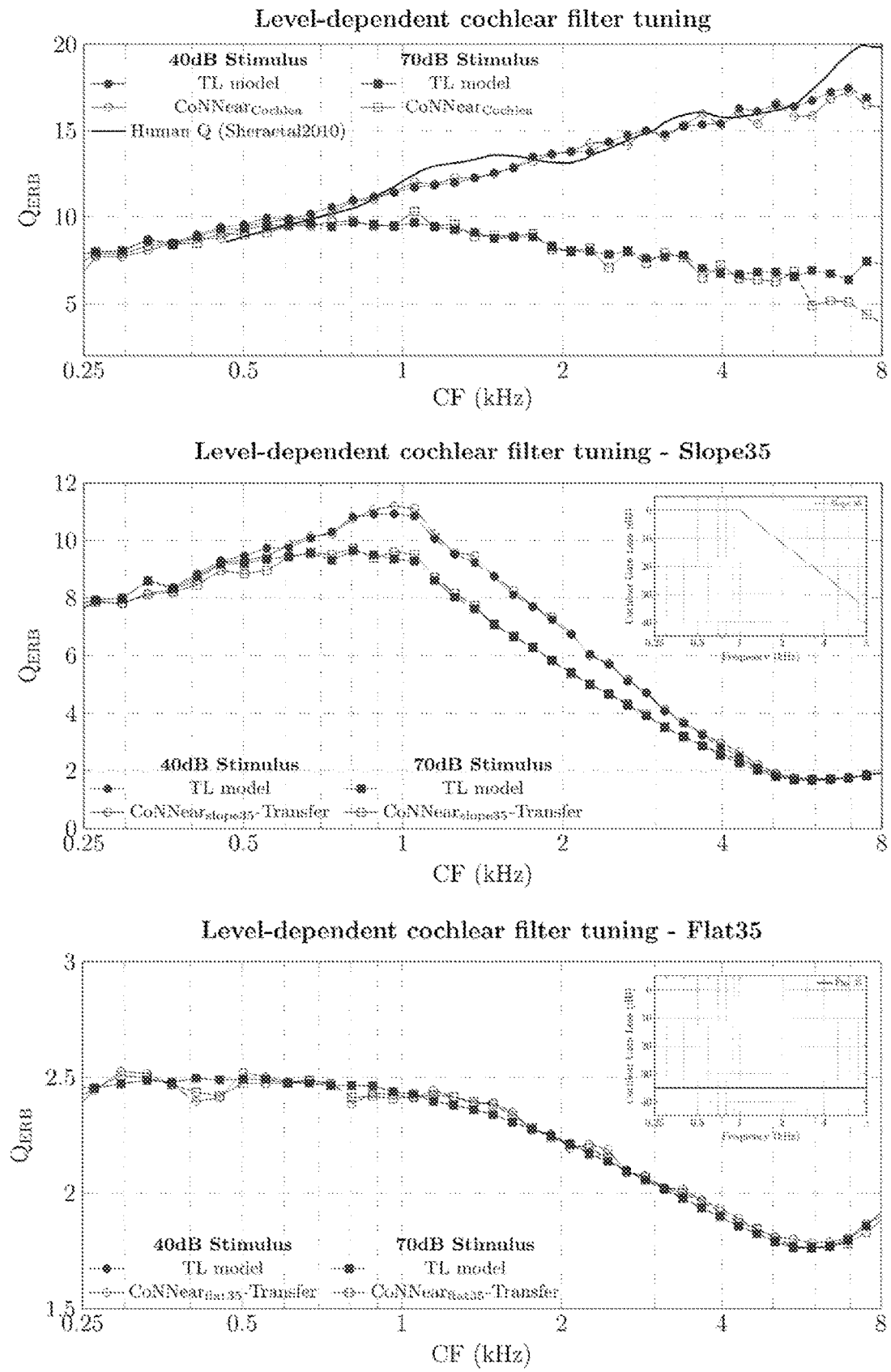
FIG. 16 shows an evaluation of different hearing-impaired cochlear processing models.

FIG. 16 shows an evaluation of different hearing-impaired cochlear processing models. The tuning of cochlear BM filters ($Q_{ERB}$) are described here as a function of CF for the reference TL-model and compared to the CoNNear model simulations. Reference experimental human $Q_{ERB}$ estimates are also shown. The top panel shows simulations for the normal-hearing model and the middle and bottom panel show simulations for hearing-impaired models corresponding to the pure-tone audiograms depicted in the insets.

Figure 10:
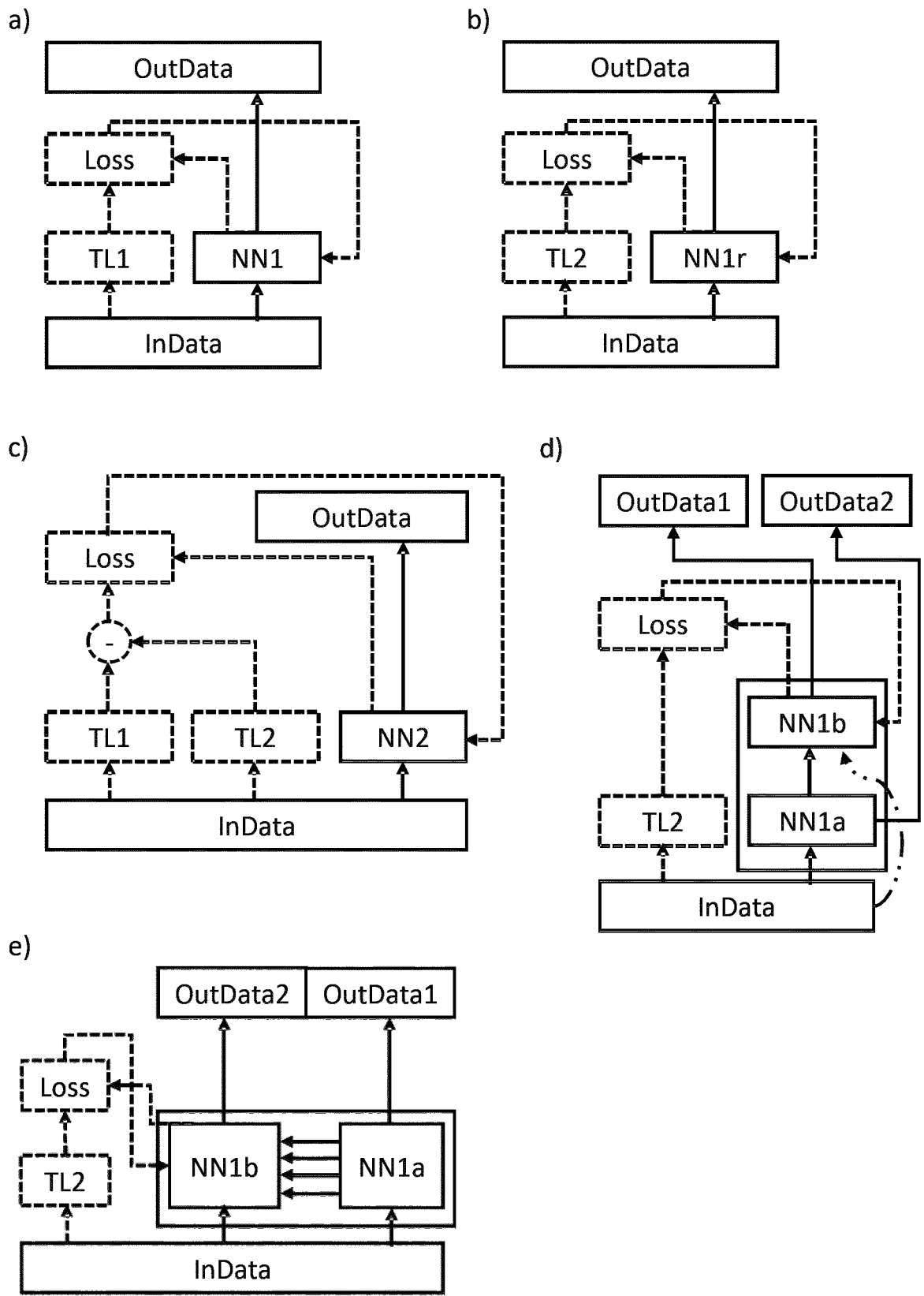
FIG. 10 illustrates different training methods for determining neural network weight parameters in accordance with embodiments of the present invention. The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention.

Various methods of training, retraining and (lateral) training of extensions to the trained neural network are now described with reference to FIG. 10. Solid lines in FIG. 10 refer to functional units or signal connections that are active during both (re)training and testing/execution, whereas dashed lines refer to functional units or signal connections that are only active during (re)training, but are inactive or removed during testing/execution. Dashed-dotted lines refer to optional input connections. In the following examples, each reference to BM processing may also be replaced by alternative types of cochlear processing, such as IHC processing (e.g. using an inner-hair-cell receptor potential model), ANF processing (e.g. using an auditory-nerve-fiber model), or combinations thereof. Each step referring to BM processing may also be performed by alternative types of cochlear processing, such as IHC processing or AN processing, mutatis mutandis.

Case a), as an example, illustrated the previously described training of a neural network for emulating cochlear processing, in this specific example cochlear BM processing (but alternatively also IHC processing or AN processing), NN1, using a transmission-line BM model TL1 as validation model and a loss function, Loss, as error metric. The input data (In Data) may correspond to speech signals, e.g. speech signals from a speech corpus such as TIMIT, during (re)training, and may correspond to auditory stimuli (audio samples, click tones, pure tones, etc.) during testing/execution. The output data (OutData) generated by the neural network NN1, when trained, comprises N output sequences associated with N distinct center frequencies of a tonotopic map, e.g. the Greenwood map.

In case b), the trained neural network for cochlear processing NN1 is (quickly) retrained with a different validation model TL2, e.g. a transmission-line model TL2 that models a hearing impairment related to OHC damage. Alternatively, TL2 could refer to an IHC or ANF model where impairments of presbycusis (IHC) and/or cochlear synaptopathy/deafferentation can be simulated respectively. The retrained neural network, NN1r, then generates N output sequences that are associated with N distinct center frequencies of the same tonotopic map, e.g. the Greenwood map, but the output samples of which are not reflecting the basilar-membrane vibrations of a normal hearing person but of a hearing impaired person. It is also possible to add a noisy signal or a signal distortion (e.g. due to signal acquisition distortions by a microphone) to the input signals of the neural network NNr and train it to perform a noise removal behavior or a signal restoration (distortion compensation).

Case c) describes a training scenario, in which a trained neural network NN1, or an untrained, new neural network for cochlear processing is trained with a combination of two validation models TL1 and TL2. For instance a difference between the output sequences generated by a first transmission line model TL1 for a normal hearing person and a second transmission line model TL2 for a hearing impaired person is determined ("−") and used as a target sequence for training of the neural network NN2. The neural network NN2, when trained, generates output sequences that correspond to corrections of a tonotopic map. These corrections may be readily used in a hearing device to correct an acquired, sampled audio signal so as to compensate the hearing impairment.

Figure 13:
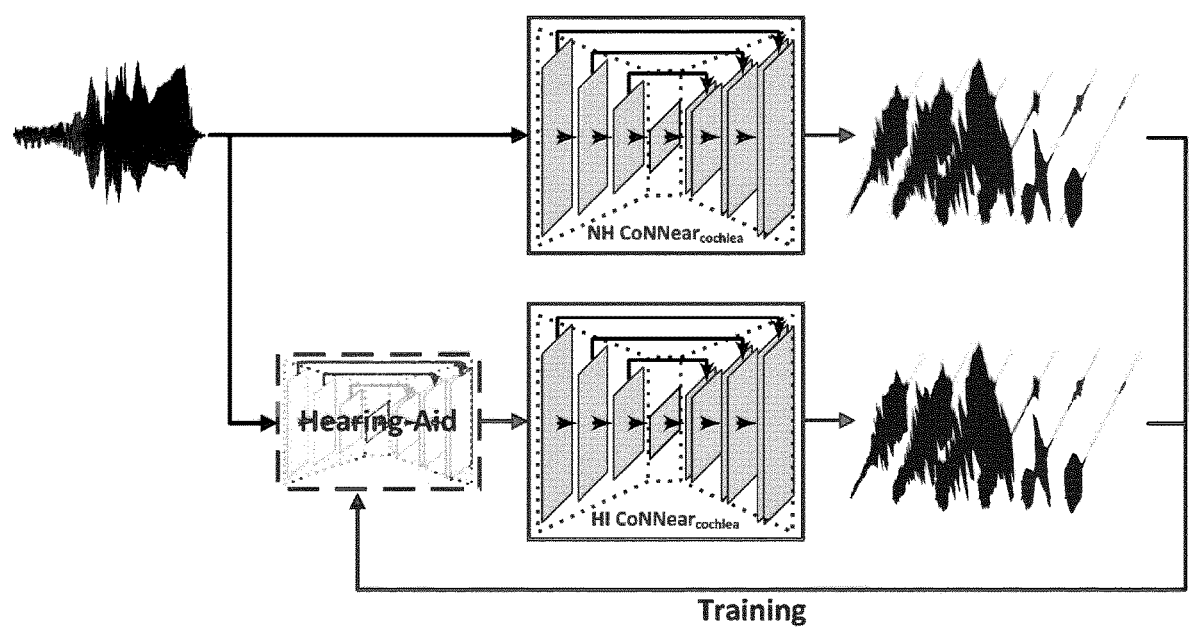
FIG. 13 illustrates a closed-loop approach for the design of a compensation-strategy for hearing-impairment. Here, simulation outcomes from a normal and hearing-impaired CoNNear model are compared to inspire a neural network signal processing algorithm which brings the hearing-impaired response closer to the normal-hearing response.

Due to its nature, the present models as described herein typically consist of highly nonlinear but parallel operations. This gives the advantage of significantly speeding up the computations when implemented on a dedicated chip, compared to the computation of complex mathematical, feed-forward expressions. At the same time, these operations are differentiable, which means that the neural network can be trained to back-propagate to the solution that in other cases would be impossible to reach. Therefore, in some embodiments, the method as described herein, and embodiments thereof, is used in a closed-loop compensation approach. For example, using a 'reference' neural network that can describe a normal-hearing auditory periphery and a corresponding hearing-impaired neural network, a 'hearing-aid' neural-network model can be trained to process the auditory input and compensate for the degraded output of the hearing-impaired model (as illustrated in FIG. 13). This individual 'hearing-aid' model will produce a signal that can match (or partially match) the output of a specific hearing-impaired cochlea to the output of the 'reference' normal-hearing cochlea. In some embodiments, the hearing-aid model is trained to minimize a specific metric, such as the absolute or squared difference between the two other models, or more complex metrics that are indicative of the degraded hearing ability.

Using the closed-loop approach, once the exact auditory profile of hearing loss is estimated for an individual, an individualized hearing-aid model can be developed that can accurately compensate for the specific hearing impairment. In some embodiments, the method comprises the step of developing an individualized hearing-aid model, preferably using the closed-loop approach as described herein. Such a hearing impairment profile can include outer-hair-cell damage, inner-hair-cell damage, cochlear synaptopathy, or even combinations of hearing loss in all different stages of the auditory periphery. Using sensitive metrics based on otoacoustic emissions (OAEs) and auditory-evoked potentials (AEPs), individualized models can be built that can account for individual synaptopathy and hair-cell damage aspects. Therefore, preferably, the individualized model comprises both synaptopathy and hair-cell damage. The developed neural network model of the auditory periphery can also be of help in this step, by providing a much faster way to cluster experimental data to simulated outputs so that an individualized profile of hearing loss can be built.

The choice of optimization metric has an impact on this closed-loop compensation. The minimization of the difference between the outputs of the normal-hearing and hearing-impaired models, as used in some embodiments, might not be always desirable or even possible, considering the complexity of these representations. In some embodiments, it may be opted to train the hearing-aid model to compensate for a single aspect of hearing damage (e.g. outer-hair-cell damage or synaptopathy) at several or all tonotopic frequencies. In some other embodiments, the hearing-aid model can be trained to optimally restore the generators of auditory evoked potentials, in which case summed cochlear responses across a range of simulated frequencies are used to determine the parameters of the hearing-aid model. In some other embodiments, simulated cochlear responses using the methods as described herein are used as an input to models of brainstem and cortical processing such that additional auditory evoked potential features can be simulated and used to determine the parameters of the hearing-aid model. In some other embodiments, the hearing-aid model is trained to process the auditory signal so that the 'reference' performance of normal-hearing subjects can be reached for a perceptual task such as speech intelligibility. In this case, a task-optimized speech 'back-end' is connected to the outputs of the normal-hearing and hearing-impaired cochlear models (i.e., 'front-ends') which will simulate the performance of listeners in different tasks. The outputs of the back-end can then be used to train a hearing-aid model which minimizes the difference between the hearing-impaired and normal-hearing performance. The front-end can be the cochlear model as described herein or the cochlear model as described herein connected to models of auditory brainstem/cortical processing. The task-optimized back-end can be a NN-based automatic-speech-recognition (ASR) system. In some embodiments, as a next step, noise or reverberation is introduced to the auditory signals to generalize the performance of these models in more realistic scenarios. In this case, a NN-based noise/reverberation suppression model can also be added as an intermediate step between the front-ends and the back-ends.

Case d) describes how an extension or previously inactive (e.g. bypassed) portion NNb of the neural network model is trained with a modified validation model TL2, e.g. a model for the cochlear processing of a hearing impaired person. The other portion shown, NNa, corresponds to the trained neural network NN1 that has been the result of training with an unmodified validation model TL1, e.g. transmission line model TL1 for a normal hearing person, and an inactive extension NNb. As a result, the larger neural network comprising both portions NNa and NNb is capable of generating output sequences the output samples of which correspond to cochlear responses (which can include BM vibration, IHC receptor potentials and ANF firing patterns), for example basilar membrane vibrations, of a normal hearing person and a hearing impaired person, respectively (e.g. degradation or partial hearing loss for the same person over time). A difference between both outputs may be formed as a correction signal.

In case e), the extended or previously inactive portion NNb of the larger neural network (NNa and NNb) is not connected sequentially to the previously trained portion NNa, but is arranged parallel thereto and is receiving multiple lateral inputs associated with the multiple extracted features at different scales for the trained neural network NN1 as portion NNa. The lateral connections between the two portions NNba and NNb have a similar function as the shortcut connections within a single neural network.

In a further aspect, the present invention also relates to computer program code or computer-readable storage media that comprise instructions for executing, on a computer or other processing device, the methods described hereinabove. The computer program code may be made available for download from the Internet, or may be made available to the user via a network connection, e.g. through a server-client application, a cloud computing application, a distributed computing application, etc. The computer program code itself may be distributed on several interconnected computers; it may be made available permanently (e.g. for permanent storage) or temporarily (e.g. during runtime only). A computer-readable storage media comprising the instructions may include any non-transitory memory device such as memory (flash) cards, hard drives, optical storage discs, USB devices, ROM, static RAM, flash memory RAM, etc.

The present invention also relates to a data processing device adapted for carrying out the steps of emulating cochlear processing, for example BM vibration, IHC or ANF processing, and optionally the steps related to the training of a neural network in accordance with embodiments of the invention. The data processing device is preferably provided as a single processor, e.g. as a special purpose ASIC chip in compact hearing devices, but may also be provided as a plurality of communicating processors, e.g. many cores or processors of a distributed computing device or system. The processing device also comprises input means for receiving at least one input sequence indicative of an auditory stimulus, e.g. an input buffer, shift register, or I/O interface for receiving data streams, and a plurality of multiply-and-accumulate units for performing convolution operations between the convolutional filters of a convolutional layer and the inputs to the convolutional layer. A memory unit of the data processing device stores at least the trained neural network weights.

The training and inference passes of a neural network according to embodiments of the invention may be accelerated using special hardware, e.g. graphical processing units (GPUs) or a systolic array of processing elements operable for flexible data flow mappings.

Figure 7:
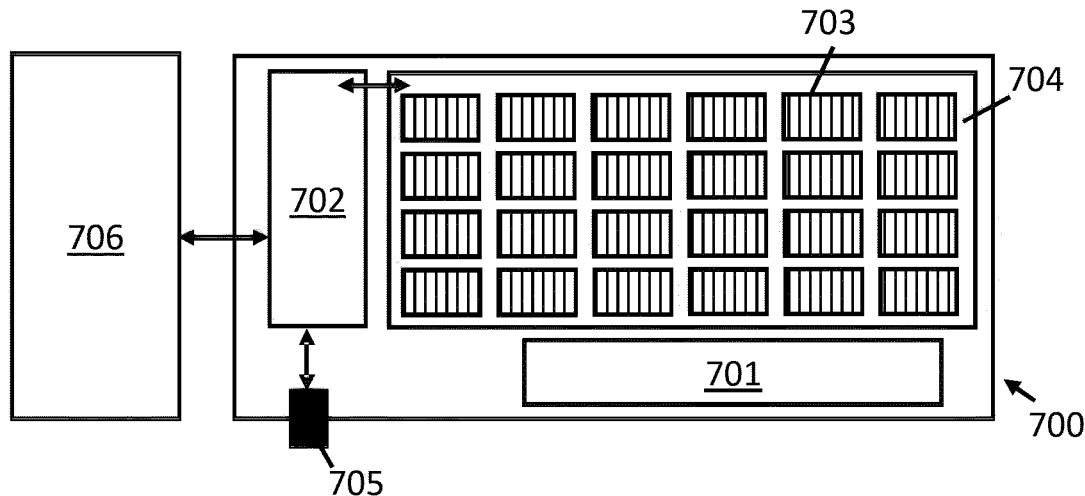
FIG. 7 schematically shows an example of a processing device according to the present invention.

With reference to FIG. 7, an example of a processing device according to some embodiments is now described briefly. The processing device 700, which may be an integrated semiconductor device (e.g. chip), may comprise a control unit 701, a global buffer 702, an array 703 of processing elements 704, and multiple data input/output connectors for receiving or sending data, for example a connector 705 for receiving/sending data comprising sequences of time-sampled signals, e.g. for receiving sensor time series data from one or more microphones or sending output sequences generated by the neural network implementation to an acoustic transducer. The network weight parameters required for performing an inference pass of the neural network implementation may be stored on an external memory unit 706 with large storage capacity (e.g. DRAM, SRAM, non-volatile storage device) and can be transferred to the processing device 700 on request, e.g. the control unit 701 issuing a memory read access command. At least one input sequence indicative of an auditory stimulus may be received for processing by the neural network at the connector 705 or may be retrieved from the external memory unit 706. Chunks of received neural network weight parameters and input sequences may be buffered in the global buffer 702 of the processing device 700 before being directed to specific processing elements 704 of the array 703 by respective commands of the control unit 701. The array 703 may be configured as a systolic array for enabling massively parallelized, distributed computations, e.g. the convolutions between layer inputs and convolutional filters of the layer are parallelized on the systolic array. The systolic array has the advantage that the partially processed data is moving across the array so that new, unprocessed data can be fed to the systolic array simultaneously. Each processing elements 704 may comprise logic that is capable of performing a multiply-and-accumulate operation. It is an advantage that the processing elements 704 only require little functionality and memory (e.g. registers) so that a large number of them can be arranged on the processing device, e.g. chip. Moreover, the processing elements 704 may store a neural network weight parameter during many computation cycles so that it is efficiently reused, which leads to less memory access cycles and latency, and also to energy savings that are important for battery-driven, portable devices. Known data flow mappings may be provided to further improve the usage efficiency of the array 703 and further reduce the energy cost, e.g. provide a row-stationary data flow. The accumulated, processed data flows are read out at an edge of the array 703 and are stored in the global buffer 702, or, if further processing is not required, may be sent to the external memory unit 706 or applied to the connector 705.

The processing device 700 may perform the data access and processing steps in a pipelined fashion to increase throughput. Likewise, input sequences may be processed in batches by the processing device 700 to further improve the throughput and reduce a delay caused by a frequent memory read/write operation. Batch processing of input data may also be advantageous in web-based or cloud-based applications accessed by a large number of users, e.g. many requests of users to run a speech recognition algorithm may be bundled for which the processing device is used as a preprocessing module. The processing device 700 may provide a data flow mapping which supports tensor convolutions as well as multiple layer input map/layer output map shapes and sizes.

For the processing device 700 in FIG. 7, the memory hierarchy and the systolic array architecture lead to important energy cost reductions and allow for highly parallel, low latency, and high throughput layer computations (e.g. convolutions). Combined with a reduction of the predetermined length of the input sequences at a given sampling rate (e.g. 16 kHz or 20 kHz), e.g. less than 8192 samples, e.g. less than 4096 samples, e.g. less than 2048 samples, e.g. less than 1024 samples, e.g. less than 512 samples, e.g. 256 samples per input sequence, less than 128 ms, e.g. less than 64 ms, e.g. less than 32 ms, e.g. 16 ms processing delay can be obtained (the processing rate for the systolic array or the processing device in general can be assumed to be large enough to only add a negligible delay). Hence, live or close-to-live processing of audio signal can be achieved, which has a positive impact on the hearing experience and comfort of persons wearing hearing devices, for instance hearing device in live sound recordings or hearing aids.

In a further aspect, the present invention relates to a hearing device comprising a data processing device as previously described is disclosed, and further comprising air pressure detection means for detecting a time-varying pressure signal indicative of at least one auditory stimulus, sampling means for sampling the detected auditory stimulus to obtain an input sequence comprising a plurality of input samples, and at least one transducer for converting output sequences generated by the neural network into audible time-varying pressure signals or corresponding auditory nerve stimuli associated with the at least one auditory stimulus. The hearing device preferably is an ear-worn electronic device, but is not limited thereto. Exemplary hearing devices include head-sets, hearing aids, personal amplification devices, cochlear implants, and other hearables. It can be of one of the following types: in-the-ear (ITE), behind-the-ear (BTE), receiver-in-canal (RIC), completely-in-canal (CIC). Other examples include brain computer interfaces, for example auditory evoked potentials could be monitored with an EEG-sensor to adjust/retrain the parameters of the hearing-impaired models as described herein. Alternatively, parameters for noise-reduction systems as described herein could be adjusted based on this additionally monitored auditory evoked potential signal, which can be used to minimize the processing.

Figure 4:
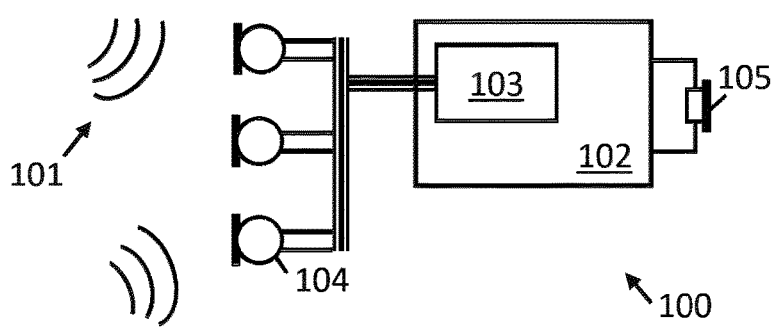
FIG. 4 describes a hearing device according to an embodiment of the present invention.

With reference to FIG. 4, a hearing device 100 is now described. The hearing device 100 includes one or more sound sensing elements, e.g. three microphones 104 or alternatively an EEG sensor. The one or more sound sensing elements, e.g. the microphone(s), have pressure detection means for detecting a time-varying pressure signal indicative of at least one auditory stimulus 101. The detected pressure signal is converted into an electrical signal for further processing by the hearing device 100. In preferred embodiments, the sound sensing element(s) are provided as microphone(s). One or more microphones may be unidirectional, pluridirectional (e.g. bidirectional, supercardioid, etc.), or omnidirectional, for detecting pressure signals 101, e.g. sound signals that are auditory stimuli, originating from one specific direction, a plurality of selected directions, or any direction, respectively. One or more microphones may be a capacitive or an inductive microphone. Typical microphones may be piezoelectric microphone, electret condenser microphone, MEMS microphone.

Moreover, the hearing device 100 comprises sampling means 103, which may be an integral part of the sound sensing element(s) or may be provided separately as one or more electronic circuits, e.g. as part of the processing device 102 as shown in FIG. 4. An electronic signal generated by each sound sensing element, e.g. microphone, is sampled subsequently in the time domain via the sampling means 103. For instance, an electronic sampling circuit, e.g. an analog-to-digital converter, of the sampling means 103 samples each electronic signal representative of the auditory stimulus at a sampling rate of 16 kHz or more, e.g. 20 kHz or more, e.g. 32 kHz or more, e.g. 44 kHz. Additionally, the sampling means may comprise a pre-amplifier, an anti-aliasing filter, or both. Alternatively or additionally, another sensor may be used, for example a sensor that measures AEP (EEG signals) such that the algorithms for noise reduction, hearing-aid signal processing can also be adjusted for.

The processing device 102 of the hearing device 100 is adapted for receiving the sampled signals in the time domain and for applying a sampled input sequence of predetermined length to a neural network in accordance with embodiments of the invention. For instance, the input layer of the neural network may be provided as a buffer or shift register which is filled by subsequent time-sampled input data and which is periodically read out in parallel, e.g. a shift register of length 2048 (or alternatively 4096 or 8192) receives input samples at a rate of 16 kHz (or alternatively 20 kHz) and all 2048 samples are read out in parallel every 2048 sampling steps, e.g. every 128 ms (or alternatively 102.4 ms). Similarly, the output layer of the neural network may comprise N vector registers of identical length, e.g. each comprising 2048 samples (or alternatively 4096 or 8192), or an equivalent arrayed memory structure, for receiving the N output sequences. Corresponding elements of the N vector registers may also be combined into a new element by a summing circuit, e.g. adder, to generate a single output sequence. Successive samples of the output sequence(s) may be retrieved also at the same sample rate, e.g. 16 kHz (or alternatively 20 kHz). Alternatively, it is possible to generate more output samples per output sequence than input samples per input sequence and retrieving them at a higher rate once they are available, e.g. generating 4096 output samples per output sequence and retrieving successive output samples at an increased rate of 32 kHz (or alternatively 40 kHz).

The processing device 102 may be an ASIC, dedicated hardware accelerator, low-latency digital audio processor, or the like, and may comprise one or more dedicated processing elements for executing a computer program code such that, when the program code is executed, the processing device 102 effectively performs the data processing steps of a neural network in accordance with embodiments of the invention. For compact hearing devices, in particular low-energy battery driven devices, the processing device is implemented as a special purpose neural network accelerator with reduced neural network weight fetching bandwidth, low-energy neural network weight storage, neural network weight reuse, etc.

According to embodiments of the invention, the neural network implemented in the data processing device 102 is emulating cochlear processing and can be trained to assist in hearing or to improve hearing quality. For instance, the neural network implemented in the data processing device 102 may be trained to remove a background noise signal from an auditory stimulus, e.g. to remove a background noise signal from ambient music or speech. Alternatively, or additionally, the neural network implemented in the data processing device 102 may be trained to improve hearing quality by filtering out a particular predefined, selectable background scenario such as traffic, street, wind, waves, restaurant, train station, car, plane, school, etc. In embodiments having regard to hearing aids, the neural network implemented in the data processing device 102 may be trained to determine and apply a correction to the acquired at least one auditory stimulus so as to compensate for a hearing impairment (e.g. partial hearing loss) in an individualized manner, e.g. based on a recent audiogram or auditory evoked potential, otoacoustic emission measurements. The applied correction then restores the impaired hearing quality of the person using the hearing aid. In yet an alternative embodiment, the neural network implemented in the data processing device 102 is used in cochlear implants for emulating cochlear processing, preferably enhanced by emulating also the inner hair cell and auditory-nerve processing, to enable a generation of corresponding stimuli which can directly stimulate the auditory nerve. The cochlear inner-hair-cell model in connection to the cochlear BM vibration model to generate realistic auditory nerve stimuli applied by a cochlear implant. In addition, the processing device 102 may perform further signal processing operations on the received input signals, prior to applying them to the input layer of the neural network. Such further signal processing operations may include peak clipping, impulse detection and attenuation (e.g. to prevent ear damages at too large acoustic levels), signal level normalization, and others.

A transducer 105 is also included in the hearing device 100. Output sequences generated by the processing device 102 are communicated to the transducer 105 for conversion into acoustic signals. For instance, the acoustic transducer 105 comprises an amplifier stage and a signal converter for generating an analog signal representation. The acoustic transducer 105 may further comprise an output shaping filter. Amplified signal are then output by the acoustic transducer 105 via a speaker or acoustic wave generator, e.g. a speaker placed in the external ear canal generates sound waves directed to the middle ear or an acoustic wave generator (e.g. vibrator) generates vibrations that are applied to the skull bone behind the ear in bone-anchored hearing aids or opto-acoustic stimulation. In an alternative embodiment, the transducer comprises electrodes for applying auditory nerve pulses in accordance with the output sequences generated by the processing device directly to the auditory nerve. Such alternative embodiment is particularly suited for cochlear implants. Alternatively, neural pulses or signals can be generated for deep-brain-stimulation.

The group of elements in FIG. 4, i.e. the sound sensing element(s), e.g. the microphone(s) 104 (and/or other sensor such as an EEG sensor), the sampling means 103, the processing device 102, and the acoustic transducer 105 may be interconnected by wire connections or by a wireless (network) connection, e.g. by RF signals. This is useful, for example, in sound record studios in which the pickup of sound and the sound mastering/mixing happens in different, acoustically isolated rooms.

Optionally, a hearing device according to some embodiments of the invention also comprises a telecoil for direct inductive coupling to a (mobile) telephone or an assistive listening system. The telecoil strongly suppresses acoustic feedback signals which may occur during the acoustic coupling of the hearing device to an external device.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Figure 2:
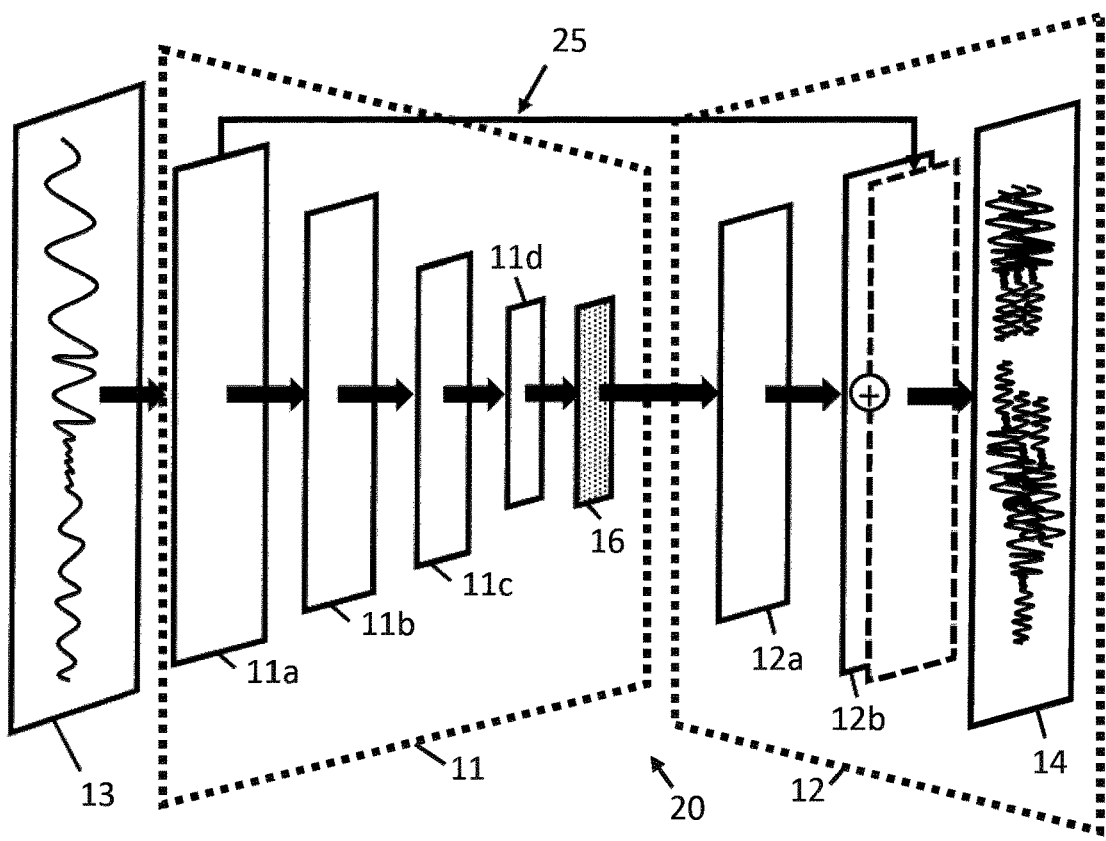
FIGS. 2 and 3 illustrate examples of a neural network with a different number of convolutional layers in the encoder and the decoder and different shortcut connections as can be used for emulating cochlear processing according to the present invention.

For example, it is possible to operate the invention in an embodiment with a neural network as shown in FIG. 2. The neural network 20 in FIG. 2 differs from the neural network referred to in FIG. 1 in that the number of convolutional layers of the encoder 11, e.g. the four convolutional layers 11a-d of the neural network 20, is not equal to the number of convolutional layers present in the decoder 12, e.g. the three convolutional layers 12a-b and 14, the last convolutional layer 14 also operating as the output layer 14 of the neural network 20. Besides, shortcut connections 25, in this particular embodiment, are arranged between the first convolutional layer 11a of the encoder 11 and the last convolutional layer 14 of the decoder 12 only.

Moreover, the encoder 11 is connected to the decoder 12 via a supplementary dense layer or fully connected layer 16, e.g. a dense layer or fully connected layer having the same filter output dimension as the preceding convolutional layer 11d of the encoder but having depth one. Such a dense or fully connected layer may be useful for learning additional encoded features which are not shift-invariant or of global nature (e.g. maximal size receptive field). If this supplementary dense layer or fully connected layer 16 is inserted at the tip of the pyramidal encoder 11, the number of neural network weights associated with this dense layer are advantageously reduced.

Figure 3:
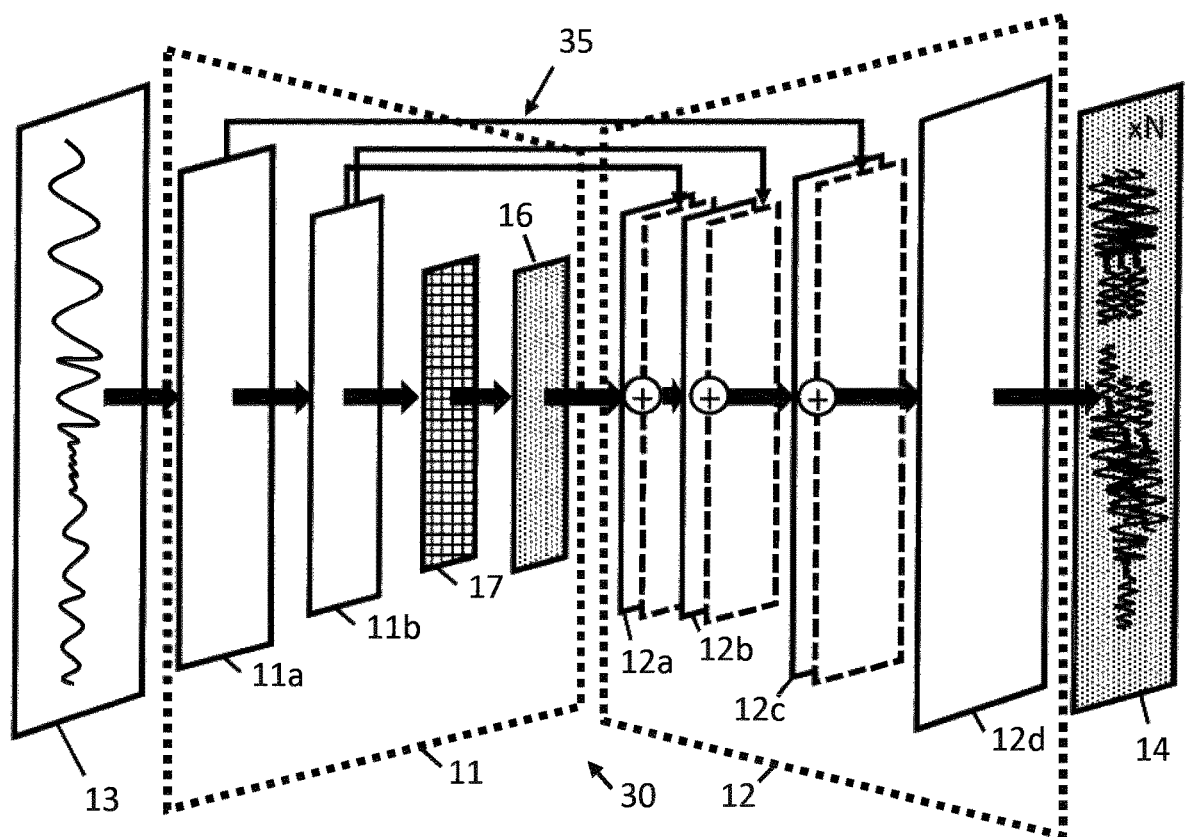

With reference to FIG. 3, a neural network 30 of yet a different embodiment is illustrated, which differs from the neural network in FIG. 1 in that the number of convolutional layers of the encoder 11, e.g. the two convolutional layers 11a-b of the neural network 30, is not equal to the number of convolutional layers present in the decoder 12, e.g. the decoder's four convolutional layers 12a-d. Moreover, the encoder 11 comprises supplementary layers 17, 16 through which it is connected to the decoder 12. As for the previous embodiment in FIG. 2, the supplementary layer 16 of the neural network 30 can be a dense or fully connected layer. In this particular embodiment, the other supplementary layer 17 of the neural network is provided as a pooling layer, e.g. a maximum or average pooling layer of size two and stride two, which effectively enables downsampling much like a convolutional layer of the encoder 11 having same stride. This is an example of replacing a convolutional layer of the encoder by a pooling layer of same stride to achieve similar downsampling of the layer input, but with the difference that the neural network weights of a convolutional layer are trainable and pooling layer filtering is not. Therefore, a reduction of neural network weights is obtainable if a loss of accuracy for the generated output sequences is still tolerable. A threshold value for tolerable accuracy generally depends on the particular application that is targeted. For example, the use of a neural network with less weights, e.g. by replacing one or more convolutional layers of the encoder by pooling layers, may lead to a reduced level of accuracy which is still tolerable for speech recognition applications for which the neural network acts as a speech preprocessing module but which is intolerable for pure cochlear processing applications, e.g. in hearing devices. The dense or fully connected layer 16 may partially compensate, or overcompensate, for the reduction in neural network weights caused by the pooling layer 17 inserted into the neural network 30 instead of another convolutional layer.

Besides, the decoder 12 of the neural network 30 comprises four convolutional layers 12a-d, three of which—the convolutional layers 12a, 12c-d—are configured as transposed convolutional layers to perform an upsampling operation on the layer inputs so as to invert the total downsampling effect of the encoder 11. The additional convolutional layer 12b has stride one to reproduce the same layer output size (e.g. the length/size of the activation maps in the temporal direction, not depth) as the preceding convolutional layer 12a and thus has the same (apparent) stride with respect to the compressed input. This guarantees that the stride for consecutive convolutional layers of the decoder 12 is increasing, even though this increase is not strictly monotonic but merely monotonic.

For this alternative embodiment, the output layer 14 of the neural network 30 is not forming part of the decoder 12, but is directly connected thereto. Also, the output layer 14 in this example is not provided as a convolutional layer, although this is an obvious alternative (e.g. convolutional layer with stride one or with stride two combined with a two times faster sampling rate for the generated output sequences, for instances, in digital audio processing applications), but as N distinct further dense or fully connected layers, each having a same output dimension (i.e. the number of neurons), which preferably is selected so as to be equal to the predetermined length of the input sequence.

It is also apparent from FIG. 3 that the shortcut connections 35 are such that the inputs to one of the convolutional layer of the encoder 11, e.g. to convolutional layer 11b, are directly forwarded as additional inputs to two distinct convolutional layers of the decoder 12, e.g. to the convolutional layers 12a-b, wherein the additional inputs are combined with the regular inputs obtained from outputs of the preceding layer, e.g. element-wise summed or element-wise summed and nonlinearly transformed.

Embodiments of the present invention have been described for emulating cochlear processing, for example BM, IHC or ANF processing of auditory stimuli, yet the described embodiments are not restricted thereto. Particular embodiments, for instance, may additionally emulate processing by the pinna, the external auditory canal, the tympanic membrane, the middle ear, etc., or may include further effects such as bone conduction, to yield a more extended emulation of the auditory system. This may be achieved by extending the reference model underlying the trained neural network approximating the same to include a biophysically correct model of the pinna, the middle ear, specific brainstem, midbrain and cortical neurons, etc., e.g. a pinna model coupled to a middle ear model for which the outputs are inputs to a cochlear transmission line model previously described. The cochlear transmission line-based BM models may further be inputs to analytical or NN-model descriptions of brainstem, midbrain and cortical auditory processing.

The cochlear BM vibration model may be used as input to an IHC receptor potential model and to an IHC-ANF synapse model, as set out below.

Inner-Hair-Cell Receptor Potential Model:

Experimentally extracted IHC parameters for analytical model descriptions of their processing typically rely on in-vitro, whole-cell patch clamp measurements of the cellular structures and channel properties. These traditional, non-NN based, models describe the nonlinear and frequency-dependent transduction from cochlear BM vibrations which are sensed by the IHC stereocilia and transformed in the IHC receptor potential. Examples of such models are known in the art. In some embodiments, the IHC model estimates the vibrations of the IHC stereocilia based on the mechanical drive to the IHC and predicts the IHC receptor potential which drives synaptic transmission to the ANF synapses and neurons, several models include the basolateral outward K+ currents to accurately capture the time-constants associated with the IHC receptor potential.

We invented a NN-based IHC model which follows the general encoder-decoder model in FIG. 3, and which follows the training procedure visualized in FIG. 13 and uses the Verhulst et al. 2018 cochlear TL model (BM vibration and IHC processing modules) to generate the training data. The TIMIT speech corpus (250 sentences, levels of 70 and 130 dB SPL) was given to the cochlear TL model and N=201 simulated outputs of the BM vibration and IHC receptor potential outputs were used as input and output datasets respectively to determine the exact architecture and hyperparameters of the NN-based IHC model. The extracted TL-model data were downsampled to 20 kHz and sliced to windows of 2048 samples with 50% overlap, with 256 context samples as input to the NN-based IHC model, the model outputs were cropped to 2048 samples. The sliced data were reduced to one-dimensional datasets, resulting in 250×201=50250 different sequences for the input and output datasets correspondingly. This was necessary because the successive stages of cochlear processing are computed on-frequency, i.e. the same operations are applied to each of tonotopic frequency section of the cochlea. Therefore, during training, the NN-based IHC module of CoNNear was designed to have a single input/output (N=1), with the sliced sequences given as one-dimensional inputs/outputs pairs. The training was performed with a batch size of 1000 one-dimensional sequences, using the Adam optimizer and a learning rate of 1e-4. The model was trained to minimize the L-1 loss between the simulated output and the output dataset.

After the training phase, the model was extended to work for an N-channel input sequence by applying the same calculated weights across this N-channel input array such that the trained IHC model module can calculate IHC potentials across all N channels corresponding to tonotopic locations along the BM. The architecture that was found to best approximate the IHC module was an auto-encoder with 6 convolution layers (3 for the encoder and 3 for the decoder) and 128 filters in each layer with a filter length of 64. Strided convolutions were used in every layer that halved the size in every step of the encoder and doubled the size in every step of the decoder respectively, in the same way as in the cochlear stage. Different nonlinear activation functions were used for the layers comprising the encoder and the decoder stages correspondingly. For the encoder, the same nonlinear function as in the BM vibration model module was used (tanh). However, because the IHC receptor potential corresponds to a voltage difference, a sigmoid nonlinear function in the decoding layers was found to better capture the reference TL model outputs and ensured that the compressive nature present in the tanh could be preserved in the possible negative value output of the inner-hair-cell receptor potential.

Figure 11:
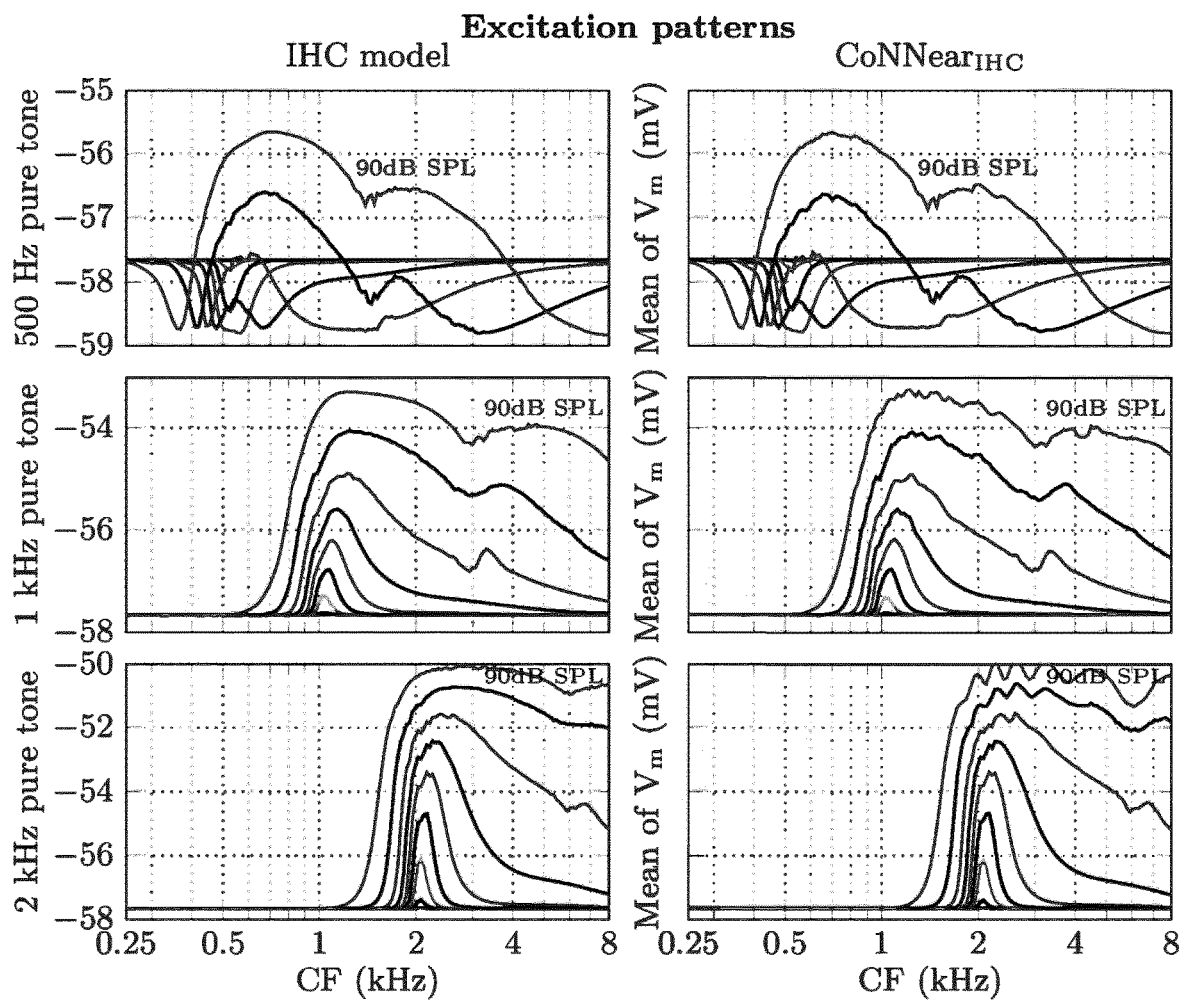
FIG. 11 illustrates IHC receptor potential excitation patterns of a neural-network cochlear model according to an embodiment of the invention (herein referred to as the CoNNear model) for pure-tone stimuli. Both BM vibration and IHC models were included to simulate the responses to 100 ms pure tones of different frequencies. For each simulated CF, the average IHC receptor potential was calculated for stimulus levels between 10 and 90 dB SPL. The CoNNear model simulations are compared to the same responses simulated using a TL-based cochlear model which contains the same processing stages.
Figure 12:
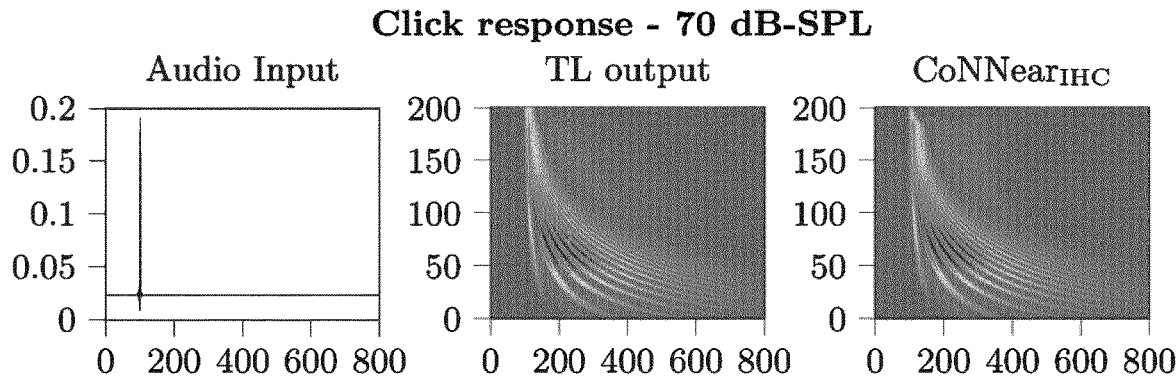
FIG. 12 illustrates IHC receptor potential responses of the neural-network cochlear model (CoNNear) to a click stimulus. CoNNear responses were compared to a reference TL-model based cochlear model which included descriptions of BM vibration and IHC transduction.

The performance of the NN-based IHC model was compared against animal data and simulations of the reference biophysical TL model using basic acoustic stimuli which were not part of the training data-set (pure tones, clicks, etc.). Simulated excitation patterns for pure-tone stimuli of different frequencies and levels as well as the response to a click stimulus are shown in FIGS. 11 and 12, respectively.

Auditory-Nerve Fiber Model

Single-unit recordings from the auditory-nerve (AN) can reliably be obtained from animal physiology and have over the years resulted in a large collection of AN responses to basic auditory stimuli in cats and small rodents. These recordings have inspired analytical model descriptions of the processing taking place in the IHC-ANF synapse and ANF neurons. These state-of-art models typically describe the ANF spikes or instantaneous firing rate resulting from the depletion and replenishment of different neurotransmitter stores and may include a three-store diffusion model modeled as a coupled set of ordinary differential equations (ODEs), which takes the IHC receptor potential as model input. Several examples of such IHC-ANF models exits and predict AN responses of the three spontaneous-rate fibers, namely high-spontaneous-rate (HSR), medium-spontaneous-rate (MSR) and low-spontaneous-rate (LSR), as known in the art. The state-of-art models contain a set of coupled (nonlinear ODEs) which are slow to compute and cannot easily be differentiated, and can hence not be embedded in backpropagating networks or real-time applications, whereas our NN-based AN model architecture allows this possibility.

We invented three NN-based models of cochlear ANF processing which each simulate the responses of different spontaneous-rate ANF types and used the same 250 TIMIT sentences for training purposes. N=201 outputs were extracted for each of the three ANF models with a sampling frequency of 20 kHz. The one-dimensional datasets were sliced to windows of 8192 samples with 50% overlap and 8192 samples context. The longer window was needed to capture the slow, exponentially-decaying time adaptation properties (in the order of 300 ms) for a step response. The training of the ANF models was done to minimize the L-1 loss between the reference cochlear TL-model ANF responses described in Verhulst et al. 2018 and the respective CoNNear ANF models. Simulated IHC receptor potentials to the TIMIT dataset served as input. The architecture that was found to best capture the responses of the three different ANF fibers consisted of up to 14 encoder/decoder convolution layers (28 layers in total). However, fewer convolution filters of shorter length (16) were necessary in each layer as compared to BM vibration model which also resulted in considerably less parameters. The deeper architecture was necessary to capture the slow adaptation properties of ANF responses, the lower number of convolutions was consistent with the lower number of coupled ODEs present in the state-of-art reference TL model. As before, strided convolutions were used that halved the size in every step of the encoder and doubled the size in every step of the decoder respectively. The compressive growth properties (and negative signal deflections) present in BM and IHC processing are not retained in ANF processing. A linear activation function could be used (i.e. a Parametric ReLU; PreLU) between the different encoder/decoder layers. The final CoNNear ANF model was validated using basic auditory stimuli (pure-tones, clicks, SAM tones etc) it did not see during training. CoNNear ANF responses were compared to animal ANF responses as well as to simulations of the ANF module of the cochlear TL model. FIG. 15 shows simulated instantaneous ANF rate responses for the reference cochlear ANF model (left) and the CoNNear model (right) for pure-tone step responses of 1 and 4 kHz. Aside from some low-level NN-noise, the CoNNear ANF module accurately captures the onset, adaptation and carrier-frequency properties of the reference model, and are in line with reference cat ANF physiology data (Kiang et al., 1965). A last example of a specific embodiment of the present invention relates to hearing-impaired CoNNear models. To develop CoNNear models which mimic an individual hearing loss at the level of cochlear processing (e.g. outer- or inner hair cell, ANF damage) we can use the training procedures described above, but start with a reference TL model which is individualized to an individual hearing damage pattern to generate the training data. Either the CoNNear models can be fully retrained using the generated training data, or a transfer-learning technique can be used for which only a subset of the training data is used to determine the hyperparameters of the specific cochlear response model which follows the same architecture as the normal-hearing CoNNear model. We show a specific example of the success of generating hearing-impaired CoNNear models for BM vibration. FIG. 16 (top panel) shows experimental tuning characteristics ($Q_{ERB}$) of human cochlear filters across the tonotopic frequencies (CF) along the BM (Shera et al. 2010) along with simulated reference TL-model which was used for training purposes (black symbols). The normal-hearing CoNNear $Q_{ERB}$ match the experimental and simulated values really well across frequency and stimulus level. In the middle and bottom panel of FIG. 16, we simulated BM vibration patterns for two OHC-damage CoNNear models. For this purpose, we used a reference TL model which matched the hearing-impaired audiograms depicted in the inset and the CoNNear training procedures described earlier. FIG. 16 demonstrates that the trained hearing-impaired CoNNear models closely match the simulations of the reference hearing-impaired TL models. Two distinct types of hearing impairment were considered: a sloping high-frequency hearing loss (Slope35, middle panel), and a flat gain loss where the outer-hair-cells were equally damaged at all tonotopic cochlear frequencies (Flat35, bottom panel). The respective corresponding hearing-impaired audiograms are shown in the insets of the two plots.

Figure 17:
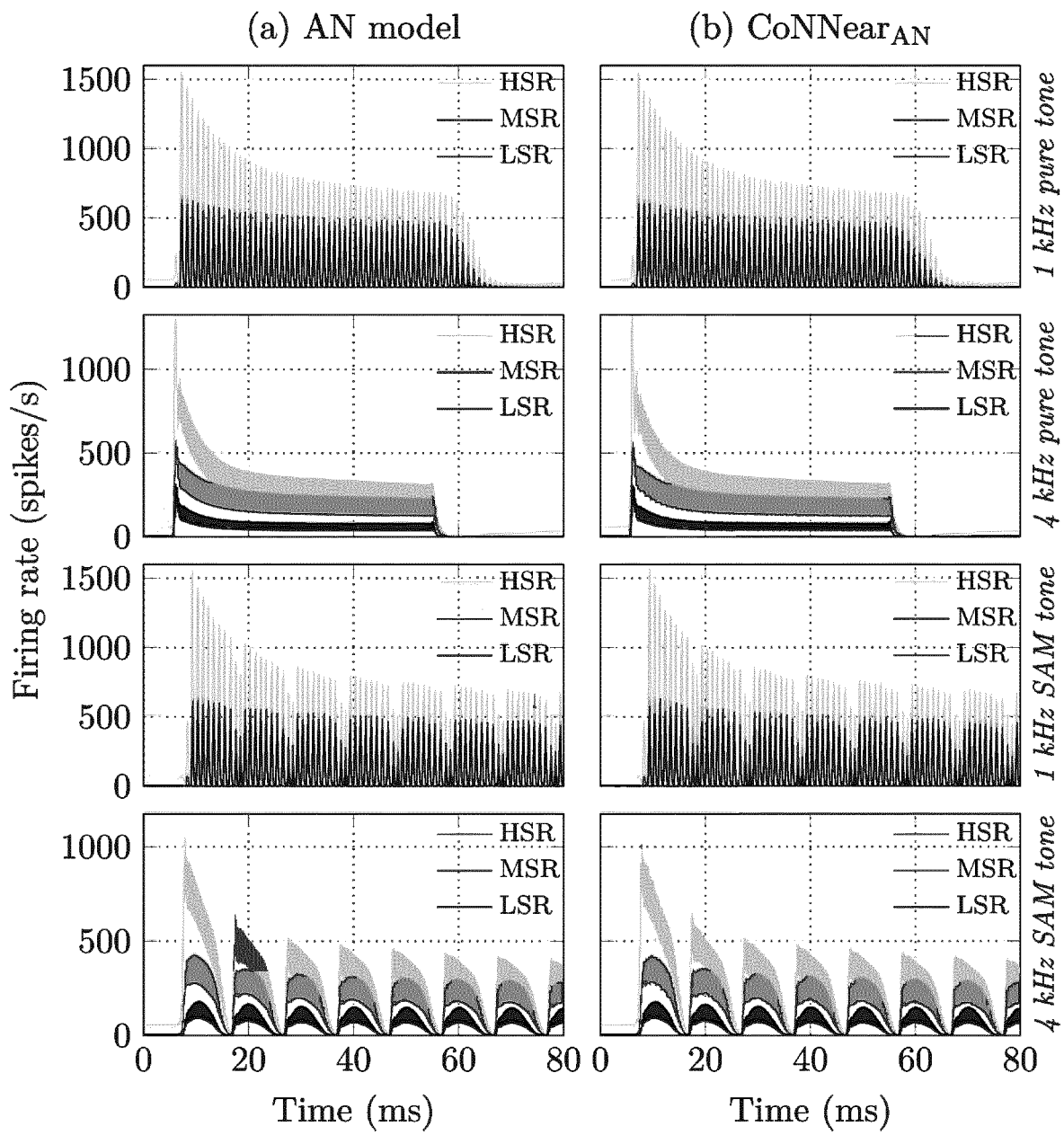
FIG. 17 provides a more elaborate version of FIG. 15, simulating the AN firing rate across time for tone stimuli presented at 70 dB-SPL, for an AN model (a) and for a model according to an embodiment of the invention (b).

FIG. 17 provides a more elaborate version of FIG. 15, simulating the AN firing rate across time for tone stimuli presented at 70 dB-SPL, for an AN model (a) which is the same as the TL model used in FIG. 15, and for a model according to an embodiment of the invention (b) CoNNear. The top, middle, and lower graphs correspond to the responses of the high-spontaneous-rate, medium-spontaneous-rate, and low-spontaneous-rate fiber models respectively, while FIG. 15 only showed the low-spontaneous-rate component of the AN stage. From top to bottom, the tone stimuli were:

1 kHz pure tone;
4 kHz pure tone;
1 kHz amplitude-modulated tone; and,
4 kHz amplitude-modulated tone.

Figure 18:
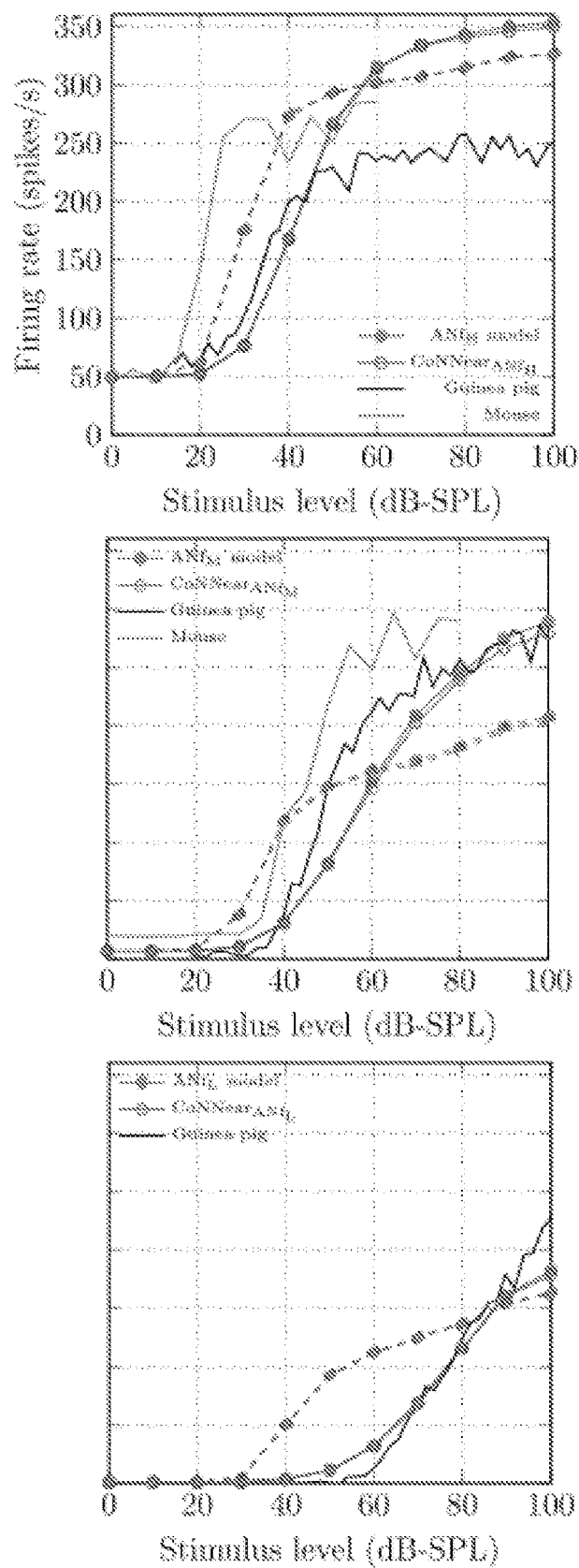
FIG. 18 illustrates simulated level-rate curves. From top to bottom, AN rate-level curves were simulated for the high-spontaneous-rate, medium-spontaneous-rate, and low-spontaneous-rate AN fiber models respectively.

FIG. 18 illustrates simulated level-rate curves. From top to bottom, AN rate-level curves were simulated for the high-spontaneous-rate, medium-spontaneous-rate, and low-spontaneous-rate AN fiber models respectively. For each ANF model, 50-ms tone stimuli were generated and presented at CFs of 1 (dashed colored) and 4 kHz (solid colored). The reference data stemmed from guinea pig (fibers with SRs of 65 spikes/s, 10 spikes/s and 0 spikes/sec at a CF of ~1.5 kHz) and mouse recordings (CF of 18.8 kHz for SR of 47.6 spikes/s and CF of 23.7 kHz for SR of 0.1 spikes/s). The CoNNear model (empty circles) is according to an embodiment of the invention. The reference model and the CoNNear model comprises three fiber models labeled ANfH, ANfM, and ANfL, for high-spontaneous-rate, medium-spontaneous-rate, and low-spontaneous-rate, respectively.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A computer-implemented method for emulating cochlear processing of auditory stimuli, the method comprising the steps of:

providing a multilayer convolutional encoder-decoder neural network (10) including
an encoder (11) and a decoder (12), each comprising at least a plurality of successive convolutional layers (11a-d; 12a-c, 14), successive convolutional layers (11a-d) of the encoder having increasing strides with respect to an input to the neural network to sequentially compress the input and successive convolutional layers (12a-c, 14) of the decoder having increasing strides with respect to the compressed input from the encoder to sequentially decompress the compressed input, each of the convolutional layer comprising a plurality of convolutional filters for convolution with an input to the convolutional layer to generate a corresponding plurality of activation maps as outputs,
at least one nonlinear unit for applying a nonlinear transformation to the activation maps generated by at least one convolutional layer of the neural network, the nonlinear transformation mimicking a level-dependent cochlear filter tuning associated with cochlear mechanics and outer hair cells,
a plurality of shortcut connections (15) between the encoder and the decoder for forwarding inputs to a convolutional layer of the encoder directly to at least one convolutional layer of the decoder,
an input layer (13) for receiving inputs to the neural network, and
an output layer (14) for generating, for each input to the neural network, N output sequences of cochlear response parameters corresponding to N emulated cochlear filters associated with N different center frequencies to span a cochlear tonotopic place-frequency map, the cochlear response parameters of each output sequence being indicative of a place-dependent time-varying vibration of a cochlear basilar membrane,
providing at least one input sequence of predetermined length indicative of a time-sampled auditory stimulus, and applying the at least one input sequence to the input layer (13) of the neural network to obtain the N output sequences of cochlear response parameters, and
optionally, summing the obtained N output sequences to generate a single output sequence of cochlear response parameters.

2. A method according to claim 1, wherein the nonlinear unit applies the nonlinear transformation as an element-wise nonlinear transformation, preferably a hyperbolic tangent.

3. A method according to claim 1, wherein a number of convolutional layer (11a-d) of the encoder (11) equals a number of convolutional layers (12a-c; 14) of the decoder (12).

4. A method according to claim 3, wherein the neural network (10) comprises shortcut connections (15) between each but the last one convolutional layer of the encoder (11) and a corresponding one convolutional layer of the decoder (12).

5. A method according to claim 4, wherein the neural network (10) comprises shortcut connections (15) between the first of the successive convolutional layers (11a) of the encoder (11) and the last of the successive convolutional layers (14) of the decoder (12).

6. A method according to claim 3, wherein the increasing strides for the successive convolutional layers of the encoder with respect to the input to the neural network is equal to the increasing strides for the successive convolutional layers of the decoder with respect to the compressed input, thereby matching each convolutional layer of the encoder with a corresponding one convolutional layer of the decoder to transpose a convolution operation of the convolutional layer of the encoder.

7. A method according to claim 1, wherein a number of samples for the at least one input sequence equals a number of cochlear response parameters in each output sequence.

8. A method according to claim 1, wherein the neural network comprises a plurality of nonlinear units for applying a nonlinear transformation to the activation maps generated by each convolutional layer of the neural network.

9. A method according to claim 1, wherein the at least one input sequence comprises a pre-context and/or a post-context portion, respectively preceding and/or succeeding a plurality of input samples indicative of the auditory stimulus, and wherein the method further comprises cropping each of the generated output sequences to contain a number of cochlear response parameters that is equal to a number of input samples of the plurality of input samples indicative of the auditory stimulus.

10. A method for determining a plurality of weight parameters associated with the neural network in the emulation method of claim 1, comprising:
providing a training dataset comprising a plurality of training input sequences, each comprising a plurality of input samples indicative of a time-sampled auditory stimulus,
providing a biophysically accurate validation model for cochlear processing, preferably a cochlear transmission line model, a degree of accuracy of which is evaluated with respect to experimentally measured cochlear response parameters indicative of place-dependent time-varying basilar membrane vibrations in accordance with a cochlear tonotopic place-frequency map,
generating N training output sequences for each training input sequence, each of the N training output sequences being associated with a different center frequency of the cochlear tonotopy map,
performing the emulation method using training input sequences to generate corresponding emulated sequences of cochlear response parameters for the neural network with respect to the same cochlear tonotopy map, and evaluating a deviation between the emulated sequences and the training output sequences arranged as training pairs, the emulated sequence and the training output sequence of each training pair being associated with a same training sequence,
using an error backpropagation method for updating the neural network weight parameters comprising weight parameters associated with each convolutional filter,
optionally, retraining the neural network weight parameters for a different set of neural network hyperparameters to further reduce the deviation, the different set of neural network hyperparameters including one or more of: a different nonlinear transformation applied by the at least one nonlinear unit, a different number of convolutional layers in the encoder and/or decoder, a different number of convolutional filters in any one convolutional layer of the neural network, a different length as the predetermined length for the input sequence, a different configuration of shortcut connections.

11. A method according to claim 10, further comprising the steps of providing a modified validation model reflecting cochlear processing subject to a hearing impairment, and retraining the neural network weight parameters for the modified validation model or a combination of the validation model and the modified validation model.

12. A data processing device comprising means for carrying out the method steps of claim 1, the data processing device further comprising:
input means for receiving at least one input sequence indicative of an auditory stimulus,
a plurality of multiply-and-accumulate units for performing convolution operations between the convolutional filters of a convolutional layer and the inputs to the convolutional layer,
a memory unit for storing at least the neural network weight parameters.

13. A hearing device (100) comprising the data processing device (102) of claim 12, and further comprising:
a pressure detection means (104) for detecting a time-varying pressure signal indicative of at least one auditory stimulus,
sampling means (103) for sampling the detected auditory stimulus to obtain an input sequence comprising a plurality of input samples, and
at least one transducer (105) for converting output sequences generated by the neural network into audible time-varying pressure signals, basilar membrane vibrations, or corresponding auditory nerve stimuli associated with the at least one auditory stimulus.

14. A computer program comprising instructions which, when the program is executed by a computer, perform the method steps of claim 1.

15. A computer-readable medium comprising instructions which, when the program is executed by a computer, perform the method steps of claim 1.

* * * * *